United States Patent [19]
Heidtmann et al.

[11] Patent Number: 6,080,575
[45] Date of Patent: Jun. 27, 2000

[54] NUCLEIC ACID CONSTRUCT FOR EXPRESSING ACTIVE SUBSTANCES WHICH CAN BE ACTIVATED BY PROTEASES, AND PREPARATION AND USE

[75] Inventors: Hans Heinrich Heidtmann; Rolf Mueller; Hans-Harald Sedlacek, all of Marburg, Germany

[73] Assignee: Hoechst Aktiengesellschaft AG, Germany

[21] Appl. No.: 09/008,308

[22] Filed: Jan. 16, 1998

[30] Foreign Application Priority Data

Jan. 16, 1997 [DE] Germany .......................... 197 01 141

[51] Int. Cl.$^7$ .............................. C12N 15/00; C12N 1/12; C07H 21/02
[52] U.S. Cl. ....................... 435/320.1; 435/456; 435/464; 536/23.1
[58] Field of Search .............................. 435/320.1, 252.1, 435/445, 465, 466; 536/23.1

[56] References Cited

PUBLICATIONS

Specific Chemoimmunotherapy, pp. 81–85.
M. Schmitt, et al., "Tumor–associated Proteases", *Fibrinolysis*, vol. 6, Suppl. 4, pp. 3–26 (1992).
D.W. Cottam et al., "Regulation of matrix metalloproteinases: their role in tumor invasion and metastasis (Review)", *International Journal of Oncology*, vol. 2, pp. 861–872 (1993).
Tryggvason et al. "Type IV collagenases in invasive tumors", *Breast Cancer Research and Treatment*, vol. 24, pp. 209–218 (1993).
Leto et al., "Cathespin D in the Malignant Progression of Neoplastic Diseases (Review)," *Anticancer Research*, vol. 12, pp. 235–240 (1992).
D.A. Hart, "Dysregulation of Plasminogen Activators in Cancer—Potential Role in Invasion, Metastasis and as a Prognostic Indicator", *Fibrinolysis*, vol. 6, Suppl. 1, pp. 11–15 (1992).
Albini, et al., "Tumor Cell Invasion Inhibited by TIMP-2", *Reports*, vol. 83, No. 11, pp. 775–779 (Jun. 5, 1991).
Hocman, "Chemoprevention of Cancer: Protease Inhibitors", *Minireview*, pp. 1365–1375 (1991).
Walter Troll, Ph.D., et al., "Protease Inhibitors as Anticarcinogens", *JNCI*, vol. 73, No. 6, pp. 1245–1250 (Dec. 1984).
J.M. Ray, et al., "The role of matrix metalloproteases and their inhibitors in tumour invasion, metastasis and angiogenesis", *Eur Respir J*, vol. 7, pp. 2062–2072 (1994).
Koop, et al., "Overexpression of Metalloproteinase Inhibitor in B16F10 Cells Does Not Affect Extravasation but Reduces Tumor Growth", *Cancer Research*, vol. 54, pp. 4791–4797 (Sep. 1, 1994).
Chirivi, et al., "Inhibition of the Metastatic Spread and Growth of B16–BL6 Murine Melanoma by a Synthetic Matrix Metalloproteinase Inhibitor", *Int. J. Cancer*, vol. 58, pp. 460–464 (1994).

(List continued on next page.)

*Primary Examiner*—Paula K. Hutzell
*Assistant Examiner*—Lin Sun-Hoffman
*Attorney, Agent, or Firm*—Foley & Lardner

[57] ABSTRACT

The invention relates to a nucleic acid construct for expressing an active substance which is activated by an enzyme which is released from mammalian cells, which construct comprises the following components: a) at least one promoter element, b) at least one DNA sequence which encodes an active compound (protein B) c) a least one DNA sequence which encodes an amino acid sequence (part structure C) which can be cleaved specifically by an enzyme which is released from a mammalian cell, and d) at least one DNA sequence which encodes a peptide or protein (part structure D) which is bound to the active compound (protein B) by way of the cleavable amino acid sequence (part structure C) and inhibits the activity of the active compound (protein B), and also to the use of the nucleic acid construct for preparing a drug for treating diseases.

22 Claims, 3 Drawing Sheets

OTHER PUBLICATIONS

Denhardt, et al., "Tissue Inhibitor of Metalloproteinases (TIMP, aka EPA): Structure, Control of Expression and Biological Functions", *Pharmac. Ther.*, vol. 59, pp. 329–341 (1993).

Melchiori, et al., "Inhibition of Tumor Cell Invasion by a Highly Conserved Peptide Sequence from the Matrix Metalloproteinase Enzyme Prosegment", *Cancer Research*, vol. 52, pp. 2353–2356 (Apr. 15, 1992).

Panchal, et al., "Tumor protease–activated, pore–forming toxins from a combinatorial library", *Nature Biotechnology*, vol. 14, pp. 852–856 (Jul. 1996).

McDonald, et al., "A Brief History of the Study of Mammalian Exopeptidases", *Mammalian Proteases*, vol. 2, pp. 5–19 (1986).

Pappot, et al., The plasminogen activation system and its role in lung cancer. A review., *"Lung Cancer"*, vol. 12, pp. 1–12 (1995).

Monsky, et al., "Proteases of cell adhesion proteins in cancer", *Cancer Biology*, vol. 4, pp. 251–258 (1993).

Rochefort, et al., "Protéases lysosomiales et invasion tumorale", médecine/sciences, vol. 7, pp. 30–36 (1991).

Kao, et al., "Collagenases in Human Breast Carcinoma Cell Lines", *Cancer Researc*, vol. 46, pp. 1349–1354 (Mar. 1986).

Fridman, et al., "Activation of Progelatinase B (MMP–9) by Gelatinase A (MMP–2)", *Cancer Research*, vol. 55, pp. 2548–2555 (Jun. 15, 1995).

Monsky, et al., "A Potential Marker Protease of Invasiveness, Seprase, Is Localized on Invadopodia of Human Malignant Melanoma Cells", *Cancer Research*, vol. 54, pp. 5702–5710 (Nov. 1, 1994).

Kao, et al., "Elastases in Human Breast Carcinoma Cell Lines", *Cancer Research*, vol. 46, pp. 1355–1358 (Mar. 1986).

Lundwall, "Characterization of the gene for Prostate–specific antigen, a human glandular kallikrein", *Biochemical and Biophysical Research Communications*, vol. 161, No. 3, pp. 1151–1159 (1989).

Riegman, et al., "Characterization of the Prostate–Specific Antigen Gene: A Novel Human Kallikrein–Like Gene", *Biochemical and Biophysical Research Communications*, vol. 159, No. 1 (1989).

Miszczuk–Jamska, et al., Characterization of trypsinogens 1 and 2 in two human pancreatic adenocarcinoma cell lines; CFPAC–1 and CAPAN–1, *FEBS*, vol. 294, No. 3, pp. 175–178 (1991).

Prockop, et al., "Collagens: Molecular Biology, Diseases, and Potentials for Therapy", *Annu. Rev. Biochem.*, vol. 64, pp. 403–434 (1995).

Ichijo, et al., "Molecular Cloning and Characterization of Ficolin, a Multimeric Protein with Fibrinogen– and Collagen–like Domains", *The Journal of Biological Chemistry*, vol. 268, No. 19, pp. 14505–14513 (1993).

Wetzels, et al., "Distribution Patterns of Type VII Collagen in Normal and Malignant Human Tissues", *American Journal of Pathology*, vol. 139, No. 2, pp. 451–459 (Aug. 1991).

Bellahcène, et al., "Expression of Bone Sialoprotein, a Bone Matrix Protein, in Human Breast Cancer", *Cancer Research*, vol. 54, pp. 2823–2826 (Jun. 1, 1994).

von der Mark, et al., "Laminin and its receptor", *Biochimica et Biophysica Acta*, vol. 823, pp. 147–160 (1985).

Hunt, "The Role of Laminin in Cancer Invasion and Metastasis", *Expl Cell Biol*, vol. 57, pp. 165–176 (1989).

Schmidtchen, et al., "Hydrophobic Interaction Chromatography of Fibroblast Proteoglycans", *Biomedical Chromatography*, vol. 7, pp. 48–55 (1993).

Barclay, et al., "Protein Superfamilies and Cell Surface Molecules", *The Leucocyte Antigen Facts Book*, pp. 38–87 (1993).

Pigott, et al., "The Adhesion Molecule Facts Book", pp. 1–21 (1993).

Ayad, et al., "The Extracellular Matrix Facts Book", pp. 8–16 (1994).

Oyama, et al., "Qualitative and Quantitative Changes of Human Tenascin Expression in Transformed Lung Fibroblast and Lung Tumor Tissues: Comparison with Fibronectin", *Cancer Research*, vol. 51, pp. 4876–4881 (Sep. 15, 1991).

Herlyn, et al., "Characterization of Tenascin Secreted by Human Melanoma Cells", *Cancer Research*, vol. 51, (Sep. 15, 1991).

Olson, et al., "bHLH factors in muscle development: dead lines and commitments, what to leave in and what to leave out", *Genes & Development*, vol. 8, pp. 1–8 (1994).

Arceci, et al., "Mouse GATA–4: a Retinoic Acid–Inducible GATA–Binding Transcription Factor Expressed in Endodermally Derived Tissues and Heart", *Molecular and Cellular Biology*, vol. 13, No. 4, pp. 2235–2246 (Apr. 1993).

IP, et al., "The GATA–4 Transcription Factor Transactivates the Cardiac Muscle–Specific Troponin C Promoter–Enhancer in Nonmuscle Cells", *Molecular and Cellular Biology*, vol. 14, No. 11, (Nov. 1994).

Yu, et al., "Human myocyte–specific enhancer factor 2 comprises a group of tissue–restricted MADS box transcription factors", *Genes & Development*, vol. 6, pp. 1783–1798 (1992).

Weintraub, et al., "MyoD binds cooperatively to two sites in a target enhancer sequence: Occupancy of two sites is required for activation", *Proc. Natl. Acad. Sci. USA*, vol. 87, pp. 5623–5627 (Aug. 1990).

Molkentin, et al., "Transcription Factor GATA–4 Regulates Cardiac Muscle–Specific Expression of the α–Myosin Heavy–Chain Gene", *Molecular and Cellular Biology*, vol. 14, No. 7, pp. 4947–4957 (Jul. 1994).

Dougherty, et al., "Gene Therapy–based Approaches to the Treatment of Cancer: Development of Targetable Retroviral Vectors", *Transfus, Sci.*, vol. 17, No. 1, pp. 121–128 (1996).

Huston, et al., "Protein engineering of antibody binding sites: Recovery of specific activity in an anti–digoxin single–chain Fv analogue produced in *Escherichia coli*", *Proc. Natl. Acad. Sci. USA*, vol. 85, pp. 5879–5883 (Aug. 1988).

McCafferty, et al., "Phage antibodies: filamentous phage displaying antibody variable domains", *Nature*, vol. 348, pp. 552–554 (Dec. 1990).

Jespers, et al., "Guiding the Selection of Human Antibodies from Phage Display Repertoires to a Single Epitope of an Antigen", *Bio/Technology*, vol. 12, pp. 899–903 (Sep. 1994).

Jones, et al., "Replacing the complementarity–determining regions in a human antibody with those from a mouse", *Nature*, vol. 321, pp. 522–525 (May 1986).

Lichtenstein, et al., "Definition and functional analysis of the signal/anchor domain of the human respiratory syncytial virus glycoprotein G", *Journal of General Virology*, vol. 77, pp. 109–118 (1996).

Harris, "Growth factors and receptors in cancer", *Current Opinion in Biotechnology*, vol. 2, pp. 260–268 (1991).

Callard et al., The Cytokine Facts Book.

Miettinen, et al., "Synovial Sarcoma—A Misnomer", *Am J Pathol*, vol. 117, No. 1, pp. 18–25 (1984).

Wojciak, et al., "The accumulation of inflammatory cells in synovial sheath and epitenon during adhesion formation in healing rat flexor tendons", *Clin Exp Immunol*, vol. 93, pp. 108–114 (1993).

Mirsky, et al., "Characterization of a plasma membrane protein present in non–myelin–forming PNS and CNS glia, a subpopulation of PNS neurons, perineurial cells and smooth muscle in adult rats", *Cell Tissue Res.*, vol. 240, pp. 723–733 (1985).

Coakham, et al., "Diagnosis of Cerebral Neoplasms Using Monoclonal Antibodies", *Prog. exp. Tumor Res.*, vol. 29, pp. 57–77 (1985).

McKeever, et al., "Patterns of Antigenic Expression of Human Glioma Cells", *Neurobiology*, vol. 6, Issue 2, pp. 119–145 (1991).

Nybroe, et al., "Biosynthesis of the Neural Cell Adhesion Molecule: Characterization of Polypeptide C", *The Journal of Cell Biology*, vol. 101, pp. 2310–2315 (Dec. 1985).

MacGillivray, et al., "Recombinant Genetic Approaches to Functional Mapping of Thrombin", *Annals New York Academy of Sciences*, pp. 73–79.

Cripe, et al., "Structure of the Gene for Human Coagulation Factor V", *Biochemistry*, vol. 31, pp. 3777–3785 (1992).

Jenny, et al., "Complete cDNA and derived amino acid sequence of human factor V", *Proc. Natl. Acad. Sci. USA*, vol. 84, pp. 4846–4850 (Jul. 1987).

O'Hara, et al., "Nucleotide sequence of the gene coding for human factor VII, a vitamin K–dependent protein participating in blood coagulation", *Proc. Natl. Acad. Sci. USA*, vol. 84, pp. 5158–5162 (Aug. 1987).

Yoshitake, et al., "Nucleotide Sequence of the Gene for Human Factor IX" (Antihemophilic Factor B), *Biochemistry*, vol. 24, pp. 3736–3750 (1985).

Messier, et al., "Cloning and expression in COS–1 cells of a full–length cDNA encoding human coagulation factor X", *Gene*, vol. 99, pp. 291–294 (1991).

Shibuya, et al., "Primary structure of bovine Hageman factor (blood coagulation factor XII): comparison with human and guinea pig molecules", *Biochimica et Biophysica Acta*, vol. 1206, pp. 63–70 (1994).

Que, et al., "Characterization of a cDNA Coding for Human Factor XII", *Biochemistry*, vol. 25, pp. 1525–1528 (1986).

Tripodi, et al., "cDNA sequence coding for human coagulation factor XII", *Nucleic Acids Research*, vol. 14, No. 7, pp. 3146–3147 (1986).

Chen, et al., "Molecular cloning, purification and in situ localization of human colon kallikrein", *Biochem, J.*, vol. 307, pp. 481–486 (1995).

Fukushima, et al., "Nucleotide Sequence of Cloned cDNA for Human Pancreatic Kallikrein", *Biochemistry*, vol. 24, pp. 8037–8043 (1985).

Yoshida, et al., "Prostate–Specific Antigen Activates Single–Chain Urokinase–Type Plasminogen Activator", *Int. J. Cancer*, vol. 63, pp. 863–865 (1995).

Petersen, et al., "Characterization of the Gene for Human Plasminogen, a Key Proenzyme in the Fibrinolytic System", *The Journal of Biological Chemistry*, vol. 265, No. 11, pp. 6104–6111 (1990).

Cramer, et al., "Prostate Specific Antigen Cleaves Parathyroid Hormone–Related Protein in the PTH–Like Domain: Inactivation of PTHrP–Stimulated cAMP Accumulation in Mouse Osteoblasts", *The Journal of Urology*, vol. 156, pp. 526–531 (Aug. 1996).

Forsgren, et al., "Molecular cloning and characterization of a full–length cDNA clone for human plasminogen", *FEBS letters*, vol. 213, No. 2, pp. 254–260 (Mar. 1987).

Zhang, et al., "Purification and Characterization of Different Molecular Forms of Prostate–Specific Antigen in Human Seminal Fluid", *Clinical Chemistry*, vol. 41, No. 11, pp. 1567–1573 (1995).

Schechter et al., "On the Size of the Active Site in Proteases", *Biochemical and Biophysical Research Communications*, vol. 27, No. 2, pp. 157–162 (1967).

Rosenberg, et al., "Grafting Genetically Modified Cells to the Damaged Brain: Restorative Effects of NGF Expression", *Science*, vol. 242, pp. 1575–1578 (1988).

Wolff, et al., "Grafting fibroblasts genetically modified to produce L–dopa in a rat model of Parkinson disease", *Proc. Natl. Acad. Sci. USA*, vol. 86, pp. 9011–9014 (Nov. 1989).

Racchi, et al., "Human Coagulation Factor X Deficiency Caused by a Mutant Signal Peptide That Blocks Cleavage by Signal Peptidase but Not Targeting and Translocation to the Endoplasmic Reticulum", *The Journal of Biological Chemistry*, vol. 268, No. 8, pp. 5735–5740 (1993).

Graham, et al., "A New Technique for the Assay of Infectivity of Human Adenovirus 5 DNA", *Virology*, vol. 52, pp. 456–467 (1973).

Watzke, et al., "Evidence that the Severe Clinical Phenotype Arises from a Mutation Blocking Secretion", *J. Clin. Invest.*, vol. 88, pp. 1685–1689 (Nov. 1991).

Seitz, et al., "Activators of Coagulation in Cultured Human Lung–Tumor Cells", *Int. J. Cancer*, vol. 53, pp. 514–520 (1993).

Sedlacek, et al., "Antibodies as Carriers of Cytotoxicity", pp. 114–133.

Monoclonal Antibodies in Tumor Therapy, pp. 42–49.

Lee, et al., "Cloning of the GATA–binding Protein That Regulates Endothelin–1 Gene Expression in Endothelial Cells", *The Journal of Biological Chemistry*, vol. 266, No. 24, pp. 16188–16192 (1991).

Dorfman, et al., "Human Transcription Factor GATA–2", *The Journal of Biological Chemistry*, vol. 267, No. 2, pp. 1279–1285 (1992).

Wilson, et al., "A Nonerythroid GATA–Binding Protein Is Required for Function of the Human Preproendothelin–1 Promoter in Endothelial Cells", *Molecular and Cellular Biology*, vol. 10, No. 9, pp. 4854–4862 (1990).

Lucibello, et al., "Periodic cdc25C transcription is mediated by a novel cell cycle–regulated repressor element" (CDE). *The EMBO Journal*, vol. 14, No. 1, pp. 132–142 (1995).

Winter, et al., "Making Antibodies by Phage Display Technology", *Annu. Rev. Immunol*, vol. 12, pp. 433–455 (1994).

Hoogenboom, et al., "Building Antibodies from their genes", *Rev. Fr. Transfus. Hémobiol.*, vol. 36, pp. 19–47 (1993).

Smith, "Filamentous Fusion Phage: Novel Expression Vectors That Display Cloned Antigens on the Virion Surface", *Science*, vol. 228, pp. 1315–1317 (Jun. 1985).

Saiki, et al., "Enzymatic Amplification of β–Globin Genomic Sequences and Restriction Site Analysis for Diagnosis of Sickle Cell Anemia", *Science*, vol. 230, pp. 1350–1354 (1985).

Orlandi, et al., "Cloning immunoglobulin variable domains for expression by the polymerase chain reaction", *Proc. Natl. Acad. Sci. USA*, vol. 86, pp. 3833–3837 (May 1989).

Skerra, et al., "Assembly of a Functional Immunoglobulin $F_v$ Fragment in *Escherichia coli*", *Science*, vol. 24, pp. 1038–1041 (May 1998).

Bird, et al., "Single–Chain Antigen–Binding Proteins", *Science*, vol. 242, pp. 423–425 (Oct. 1998).

Better, et al., "*Escherichia coli* Secretion of an Active Chimerical Antibody Fragment", *Science*, vol. 240, pp. 1041–1043 (May 1988).

McCafferty, et al., Phage antibodies: filamentous phage displaying antibody variable domains, *Nature*, vol. 348, pp. 552–554 (Dec. 1990).

Breitling, et al., "A surface expression vector for antibody screening", *Gene*, vol. 104, pp. 147–153 (1991).

Hoogenboom, et al., "Multi–subunit proteins on the surface of filamentous phage: methodologies for displaying antibody (Fab) heavy and light chains", *Nucleic Acids Research*, vol. 19, No. 15, pp. 4133–4137 (1991).

Barbas III, et al., "Assembly of combinatorial antibody libraries on phage surfaces: The gene III site", *Proc. Natl. Acad. Sci. USA*, vol. 88, pp. 7978–7982 (1991).

Marks, et al., "By–passing Immunization Human Antibodies from V–gene Libraries Displayed on Phage", *J. Mol. Biol.*, vol. 222, pp. 581–597 (1991).

Hawkins, et al., "Selection of Phage Antibodies by Binding Affinity Mimicking Affinity Maturation", *J. Mol. Biol.*, vol. 226, pp. 889–896 (1992).

Marks, et al., "Human Antibody Fragments Specific for Human Blood Group Antigens from a Phage Display Library", *Bio/Technology*, vol. 11, pp. 1145–1149 (Oct. 1993).

Sastry, et al., "Cloning of the immunological repertoire in *Escherichia coli* for generation of monoclonal catalytic antibodies: Construction of a heavy chain variable region–specific cDNA library", *Proc. Natl. Acad. Sci. USA*, vol. 86, pp. 5728–5732 (Aug. 1989).

Ward, et al., "Binding activities of a repertoire of single immunoglobulin variable domains secreted for *Escherichia coli*", *Nature*, vol. 341, pp. 544–546 (Oct. 1989).

Clackson, et al., "Making antibody fragments using phage display libraries", *Nature*, vol. 352, pp. 624–628 (Aug. 1991).

Mullinax, et al., "Identification of human antibody fragment clones specific for tetanus toxoid in a bacteriophage λ immunoexpression library", *Proc. Natl. Acad. Sci. USA*, vol. 87, pp. 8095–8099 (Oct. 1990).

Orlandi, et al., "Cloning imunoglobulin variable domains for expression by the polymerase chain reaction", *Proc. Natl. Acad. Sci. USA*, vol. 86, pp. 3833–3837 (May 1989).

Larrick, et al., "Rapid Cloning of Rearranged Immunoglobulin Genes From Human Hybridoma Cells Using Mixed Primers and the Polymerase Chain Reaction", *Biochemical and Biophysical Research Communications*, vol. 160, No. 3, pp. 1250–1256 (May 1989).

Marks, et al., "Oligonucleotide primers for polymerase chain reaction amplification of human immunoglobulin variable genes and design of family–specific oligonucleotide probes", *Eur J. Immunol*, vol. 21, pp. 985–991 (1991).

Hoogenboom, et al., "By–passing Immunisation Human Antibodies from Synthetic Repertoires of Germline $V_H$ Gene Segments Rearranged in Vitro", *J. Mol. Biol.*, vol. 227, pp. 381–388 (1992).

Barbas, et al., "Semisynthetic combinatorial antibody libraries: A chemical solution to the diversity problem", *Proc. Natl. Acad. Sci. USA*, vol. 89, pp. 4457–4461 (May 1992).

Nissim, et al., "Antibody fragments from a 'single pot' phage display library as immunochemical reagents", *The EMBO Journal*, vol. 13, No. 3, pp. 692–698 (1994).

Griffiths, et al., "Isolation of high affinity human antibodies directly from large synthetic repertoires", *The EMBO Journal*, vol. 13, No. 14, pp. 3245–3260 (1994).

Gram, et al., "In vitro selection and affinity maturation of antibodies from a naïve combinatorial immunoglobulin library", *Proc. Natl. Acad. Sci. USA*, vol. 89, pp. 3576–3580 (Apr. 1992).

Glaser, et al., "Antibody Engineering By Codon–Based Mutagenesis In A Filamentous Phage Vector System", *The Journal of Immunology*, vol. 149, No. 12, pp. 3903–3913 (Dec. 1992).

Balint, et al., "Antibody engineering by parsimonious mutagenesis", *Gene*, vol. 137, pp. 109–118 (1993).

Marks, et al., "By–Passing Immunization: Building High Affinity Human Antibodies By Chain Shuffling", *Bio/Technology*, vol. 10, pp.779–782 (Jul. 1992).

Low, et al., "Mimicking Somatic Hypermutation: Affinity Maturation of Antibodies Displayed on Bacteriophage Using a Bacterial Mutator Strain", *J. Mol. Biol.*, vol. 260, pp. 359–368 (1996).

Jespers, et al., "Guiding the selection of human antibodies from phage display repertoires to a single epitope of an antigen", Biotechnology, pp. 899–903 (1994) (Abstract).

Cosman, et al., "Human Macrophage Colony Stimulating Factor (M–CSF): Alternate RNA Splicing Generates Three Different Proteins that are Expressed on the Cell Surface and Secreted", *Behring Inst. Mitt.*, No. 83, pp. 15–26 (1988).

Vijaya, et al., "Transport to the Cell Surface of a Peptide Sequence Attached to the Truncated C Terminus of an N–Terminally Anchored Integral Membrane Protein", *Molecular and Cellular Biology*, vol. 8, No. 4, pp. 1709–1714 (Apr. 1988).

Brown, et al., "Redundancy of Signal and Anchor Functions in the $NH_2$–Terminal Uncharged Region of Influenza Virus Neuraminidase, a Class II Membrane Glycoprotein", *Journal of Virology*, vol. 62, No. 10, pp. 3824–3831 (Oct. 1988).

Ferguson et al., "Cell–Surface Anchoring of Proteins Via Glycosyl–Phosphatidylinositol Structures", *Ann. Rev. Biochem.*, vol. 57, pp. 285–320 (1988).

Berling, et al., "Cloning of a Carcinoembryonic Antigen Gene Family Member Expressed in Leukocytes of Chronic Myeloid Leukemia Patients and Bone Marrow", *Cancer Research*, vol. 60, pp. 6534–6539 (Oct. 1990).

Cunningham, et al., "Neural Cell Adhesion Molecule: Structure, Immunoglobulin–Like Domains, Cell Surface Modulation, and Alternative RNA Splicing", *Articles*, pp. 799–805 (May 1987).

Clissold, "A cDNA construct of tissue inhibitor of metalloproteinases (TIMP) linked to the last exon of Thy–1 confers glycophospholipid anchorage on this naturally secreted protein", *Biochem*, vol. 281, pp. 129–136 (1992).

Selvaraj, et al., "The major Fc receptor in blood has a phosphatidylinositol anchor and is deficient in paroxysmal nocturnal haemoglobinuria", *Nature*, vol. 333, pp. 565–567 (Jun. 1988).

Burrows, et al., "Vascular Targeting—A New Approach to the Therapy of Soiled Tumors", *Pharmac. Ther.*, vol. 64, pp. 155–174 (1994).

Hughes, et al., "Monoclonal Antibody Targeting of Liposomes to Mouse Lung in Vivo", *Cancer Research*, vol. 49, pp. 6214–6220 (Nov. 1989).

Maruyama, et al., "Lipid composition is important for highly efficient target binding and retention of immunoliposomes", *Proc. Natl. Acad. Sci. USA*, vol. 87, pp. 5744–5748 (Aug. 1990).

Pusztai, et al., "Growth Factors: Regulation of Normal and Neoplastic Growth", *Journal of Pathology*, vol. 169, pp. 191–201 (1993).

Augustin–Voss, et al., "Migrating Endothelial Cells are Distinctly Hyperglycosylated and Express Specific Migration–associated Cell Surface Glycoproteins", *The Journal of Cell Biology*, vol. 119, No. 2, pp. 483–491 (Oct. 1992).

Pauli, et al., "Organ–preference of metastasis", *Cancer and Metastasis Reviews*, vol. 9, pp. 175–189 (1990).

Honn, et al., "Adhesion molecules and tumor cell interaction with endothelium and subendothelial matrix", *Cancer and Metastasis Reviews*, vol. 11, pp. 353–375 (1992).

Speir, et al., "Potential Role of Human Cytomegalovirus and p53 Interaction in Coronary Restenosis", *Science*, vol. 265, pp. 391–394 (Jul. 1994).

Powelson, et al., "Monoclonal Antibodies in Organ Transplantation," *Biotech. Adv.*, vol. 11, pp. 725–740 (1993).

Rojanasakul, et al., "Targeted Gene Delivery to Alveolar Macrophages via Fc Receptor–Mediated Endocytosis", *Pharmaceutical Research*, vol. 11, No. 12, pp. 1731–1736 (1994).

Perales, et al., "An evaluation of receptor–mediated gene transfer using synthetic DNA–ligand complexes", *Eur. J. Biochem*, vol. 226, pp. 255–266 (1994).

Kristensen, et al., "Immunophenotyping in acute leukaemia, myelodysplastic syndromes and hairy cell leukaemia", *Danish Medical Bulletin*, vol. 41, pp. 52–65 (Feb. 1994).

Schranz, V., "Monoclonal Antibodies: New Diagnostic and Therapeutic Means in Acute Leukaemias", *Third Department of Medicine*, Semmelweis University Medical School, Budapest, pp. 3–12.

Drexler, et al., "The Use of Monoclonal Antibodies for the Identification and Classification of Acute Myeloid Leukemias", *Leukemia Research*, vol. 10, No. 3, pp. 279–290 (1986).

Naeim, et al., "Selection of Monoclonal Antibodies in the Diagnosis and Classification of Leukemias", *Disease Markers*, vol. 7, pp. 1–14 (1989).

Stickney, et al., "Biologic response modifiers: therapeutic approaches to lymphoproliferative diseases", *Current Opinion in Oncology*, vol. 4, pp. 847–855 (1992).

Drexler, et al., "Routine immunophenotyping of acute leukaemias", *Blut*, pp. 327–339 (1988).

Freedman, et al., "B–Cell Monoclonal Antibodies and Their Use in Clinical Oncology", *Cancer Investigations*, vol. 9, pp. 69–84 (1991).

Cross, et al., "Growth Factors in Development, Transformation, and Tumorigenesis", *Cell*, vol. 64, pp. 271–280 (Jan. 1991).

Aulitzky, et al., "Interleukins Clinical Pharamcology and Therapeutic Use", *Drugs*, vol. 48, pp. 667–677 (1994).

Moore, Malcolm A.S., "Hematopoietic Reconstruction: New Approaches", *Clinical Cancer Research*, vol. 1, pp. 3–9 (Jan. 1995).

Van Kooten, et al., "Cytokines and Intracellular Signals Involved in the Regulation of B–CLL Proliferation", *Leukemia and Lymphoma*, vol. 12, pp. 27–33 (1993).

Morrissey, et al., "Molecular Cloning of the cDNA for Tissue Factor, the Cellular Receptor for the Initiation of the Coagulation Protease Cascade", *Cell*, vol. 50, pp. 129–135 (Jul. 1987).

Scarpati, et al., "Human Tissue Factor: cDNA Sequence and Chromosome Localization of the Gene", *Biochemistry*, vol. 26, pp. 5234–5238 (1987).

Spicer, et al., "Isolation of cDNA clones coding for human tissue factor: Primary structure of the protein and cDNA", *Proc. Natl. Acad. Sci. USA*, vol. 84,. pp. 5148–5152 (Aug. 1987).

Rehemtulla, et al., "High Level Expression of Recombinant Human Tissue Factor in Chinese Hamster Ovary Cells as a Human Thromboplastin", *Thrombosis and Haemostasis*, vol. 65, pp. 521–527 (1991).

Fritzinger, et al., "Molecular cloning and derived primary structure of cobra venom factor", *Proc. Natl. Acad. Sci. USA*, vol. 91, pp. 12775–12779 (Dec. 1994).

De Bruijn, et al., "Human complement component C3: cDNA coding sequence and derived primary structure", *Proc. Natl. Acad. Sci. USA*, vol. 82, pp. 708–712 (Feb. 1985).

O'Keefe, et al., "A Novel Cleavage Product of Human Complement Component C3 with Structural and Functional Properties of Cobra Venom Factor", *The Journal of Biological Chemistry*, vol. 263, pp. 12690–12697 (1988).

Jarvis, et al., "Induction of apoptotic DNA damage and cell death by activation of the sphingomyelin pathway", *Proc. Natl. Acad. Sci. USA*, vol. 91, pp. 73–77 (Jan. 1994).

Cruciani, et al., "Antibiotic magainins exert cytolytic activity against transformed cell lines through channel formation", *Proc. Natl. Acad. Sci. USA*, vol. 88, p. 3792–3796 (May 1991).

Mountford, et al., "Internal ribosome entry sites and dicistronic RNAs in mammalian transgenesis", *TIG*, vol. 11, No. 5, pp. 179–184 (May 1995).

Morgan, et al., "Retroviral vectors containing putative internal ribosome entry sites: development of a polycistronic gene transfer system and applications to human gene therapy", *Nucleic Acids Research*, vol. 20, No. 6, pp. 1293–1299 (1991).

Kaufman, et al., "Improved vectors for stable expression of foreign genes in mammalian cells by use of the untranslated leader sequence from EMC virus", *Nucleic Acids Research*, vol. 19, No. 16, pp. 4485–4490 (1991).

Dirks, et al., "Dicistronic transcription units for gene expression in mammalian cells", *Gene*, vol. 128, pp. 247–249 (1993).

Pelletier, et al., "Internal initiation of translation of eukaryotic mRNA directed by a sequence derived from poliovirus RNA", *Nature*, vol. 334, pp. 320–325 (Jul. 1988).

Sugimoto, et al., "Efficient Expression of Drug–selectable Genes in Retroviral Vectors Under Control of an Internal Ribosome Entry Site", *BIO/Technology*, vol. 12, pp. 694–698 (Jul. 1994).

Riechmann, et al., "Reshaping human antibodies for therapy", *Nature*, vol. 24, pp. 323–327 (Mar. 1988).

Schrewe, et al., "Cloning of the Complete Gene for Carcinoembryonic Antigen: Analysis of Its Promoter Indicates a Region Conveying Cell Type–Specific Expression", *Molecular And Cellular Biology*, vol. 10, No. 6, pp. 2738–2748 (Jun. 1990).

Berling, et al., "Cloning of a Carcinoembryonic Antigen Gene Family Member Expressed in Leukocytes of Chronic Myeloid Leukemia Patients and Bone Marrow", *Cancer Research*, vol. 50, pp. 6534–6539 (Oct. 1990).

Kozak, Marilyn, "The Scanning Model for Translation: An Update", *The Journal of Cell Biology*, vol. 108, pp. 229–241 (Feb. 1989).

Lucibello, et al., "Periodic cdc25C transcription is mediated by a novel cell cycle–regulated repressor element (CDE)", *The EMBO Journal*, vol. 14, No. 1, pp. 132–142 (1995).

Zwicker, et al., "Cell cycle regulation of cdc25C transcription is mediated by the periodic repression of the glutamine–rich activators N,F–Y and Sp1", *Nucleic Acids Research*, vol. 23, No. 19 (1995).

Jacob, et al., "Potential therapeutic applications of magainins and other antimicrobial agents of animal origin", Antimicrobial peptides, pp. 197–223, (1994).

Peck–Miller, et al., "Identification of serum components that inhibit the tumoricidal activity of amphiphilic alpha helical peptides", *Cancer Chemotherapy and Pharmacology*, vol. 32, pp. 109–115 (1993).

Figure 3

Component a) | Component b)c)d)

5'— [cdc25C promoter element] — [Immunoglobulin signal sequence] — [DNA sequence for FX, mutated at amino acid position 195 (Arg is replaced with Tyr)] —3'

SEQUENCE LISTING (1) GENERAL INFORMATION:

(iii) NUMBER OF SEQUENCES: 62

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS:
      (D) TOPOLOGY: linear (ii) MOLECULE TYPE: peptide (xi) SEQUENCE DESCRIPTION: SEQ ID NO:1:

Xaa Xaa Arg Xaa
1

(2) INFORMATION FOR SEQ ID NO:2:

(i) SEQUENCE CHARACTERISTICS:
                (A) LENGTH: 68 base pairs
                (B) TYPE: nucleic acid
                (C) STRANDEDNESS: double
                (D) TOPOLOGY: linear (ii) MOLECULE TYPE: DNA (xi) SEQUENCE DESCRIPTION: SEQ ID NO:2:

AGCAGGTGTT GGGAGGCAGC AGGTGTTGGG AGGCAGCAGG TGTTGGGAGG CAGCAGGTGT      60

TGGGAGGC                                                              68

(2) INFORMATION FOR SEQ ID NO:3:

(i) SEQUENCE CHARACTERISTICS:
                (A) LENGTH: 41 base pairs
                (B) TYPE: nucleic acid
                (C) STRANDEDNESS: double
                (D) TOPOLOGY: linear (ii) MOLECULE TYPE: DNA (xi) SEQUENCE DESCRIPTION: SEQ ID NO:3:

GGCCGATGGG CAGATAGAGG GGGCCGATGG GCAGATAGAG G                         41

(2) INFORMATION FOR SEQ ID NO:4:

(i) SEQUENCE CHARACTERISTICS:
                (A) LENGTH: 5 amino acids
                (B) TYPE: amino acid
                (C) STRANDEDNESS:
                (D) TOPOLOGY: linear (ii) MOLECULE TYPE: peptide (v) FRAGMENT TYPE: internal (xi) SEQUENCE DESCRIPTION: SEQ ID NO:4:

Cys Pro Gly Arg Val
1               5

(2) INFORMATION FOR SEQ ID NO:5:

(i) SEQUENCE CHARACTERISTICS:
                (A) LENGTH: 6 amino acids
                (B) TYPE: amino acid
                (C) STRANDEDNESS:
                (D) TOPOLOGY: linear (ii) MOLECULE TYPE: peptide (v) FRAGMENT TYPE: internal (xi) SEQUENCE DESCRIPTION: SEQ ID NO:5:

Cys Pro Gly Arg Val Val
1               5

```
(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:6:

Cys Pro Gly Arg Ile
1               5

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:7:

Cys Pro Gly Arg Ile Val
1               5

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:8:

Pro Arg Phe Lys
1

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:9:

Pro Arg Phe Lys Ile
1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS:
        (D) TOPOLOGY: linear
```

```
        (ii) MOLECULE TYPE: peptide (v) FRAGMENT TYPE: internal (xi) SEQUENCE DESCRIPTION: SEQ ID NO:10:

Pro Arg Phe Lys Ile Ile
1               5

(2) INFORMATION FOR SEQ ID NO:11:

(i) SEQUENCE CHARACTERISTICS:
             (A) LENGTH: 6 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:11:

Pro Arg Phe Lys Ile Val
1               5

(2) INFORMATION FOR SEQ ID NO:12:

(i) SEQUENCE CHARACTERISTICS:
             (A) LENGTH: 5 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:12:

Arg Arg Phe Phe Leu
1               5

(2) INFORMATION FOR SEQ ID NO:13:

(i) SEQUENCE CHARACTERISTICS:
             (A) LENGTH: 6 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:13:

Arg Arg Phe Phe Leu His
1               5

(2) INFORMATION FOR SEQ ID NO:14:

(i) SEQUENCE CHARACTERISTICS:
             (A) LENGTH: 6 amino acids
             (B) TYPE: amino acid
             (C) STRANDEDNESS:
             (D) TOPOLOGY: linear (ii) MOLECULE TYPE: peptide (v) FRAGMENT TYPE: internal
```

(xi) SEQUENCE DESCRIPTION: SEQ ID NO:14:

Arg Arg Phe Phe Leu Val
1               5

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:15:

Arg Arg Phe Phe Ile
1               5

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:16:

Arg Arg Phe Phe Ile His
1               5

(2) INFORMATION FOR SEQ ID NO:17:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:17:

Arg Arg Phe Phe Ile Val
1               5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:18:

Ser Phe Ser Ile Gln Tyr Ile Val
1               5

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:19:

Gly Ser Gln Gln Leu Leu Ile Val
1           5

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:20:

Gly Ile Ser Ser Gln Tyr Ile Val
1           5

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:21:

Pro Arg Phe Lys Ile Ile
1           5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:22:

Pro Arg Phe Lys Ile Val
1           5

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS:
        (D) TOPOLOGY: linear

```
        (ii) MOLECULE TYPE: peptide (v) FRAGMENT TYPE: internal (xi) SEQUENCE DESCRIPTION: SEQ ID NO:23:

Lys Ser Arg Met
1

(2) INFORMATION FOR SEQ ID NO:24:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (v) FRAGMENT TYPE: internal (xi) SEQUENCE DESCRIPTION: SEQ ID NO:24:

Lys Ser Arg Ile
1

(2) INFORMATION FOR SEQ ID NO:25:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (v) FRAGMENT TYPE: internal (xi) SEQUENCE DESCRIPTION: SEQ ID NO:25:

Lys Met Arg Arg
1

(2) INFORMATION FOR SEQ ID NO:26:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (v) FRAGMENT TYPE: internal (xi) SEQUENCE DESCRIPTION: SEQ ID NO:26:

Lys Met Arg Ile
1

(2) INFORMATION FOR SEQ ID NO:27:

(i) SEQUENCE CHARACTERISTICS:
           (A) LENGTH: 4 amino acids
           (B) TYPE: amino acid
           (C) STRANDEDNESS:
           (D) TOPOLOGY: linear (ii) MOLECULE TYPE: peptide (v) FRAGMENT TYPE: internal
```

```
        (xi) SEQUENCE DESCRIPTION: SEQ ID NO:27:

Ile Arg Arg Arg
1

(2) INFORMATION FOR SEQ ID NO:28:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:28:

Ile Arg Arg Ile
1

(2) INFORMATION FOR SEQ ID NO:29:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:29:

Arg Ala Arg Leu
1

(2) INFORMATION FOR SEQ ID NO:30:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:30:

Arg Ala Arg Ile
1

(2) INFORMATION FOR SEQ ID NO:31:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:31:

Gln Ala Arg Phe
1
```

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:32:

Gln Ala Arg Ile
1

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:33:

Lys Leu Arg Leu
1

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:34:

Lys Leu Arg Ile
1

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:35:

Gly Gly Gly Ala Gln
1            5

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:36:

Gly Gly Gly Ala Gln Leu
    1               5

(2) INFORMATION FOR SEQ ID NO:37:

(i) SEQUENCE CHARACTERISTICS:
                (A) LENGTH: 5 amino acids
                (B) TYPE: amino acid
                (C) STRANDEDNESS:
                (D) TOPOLOGY: linear (ii) MOLECULE TYPE: peptide (v) FRAGMENT TYPE: internal (xi) SEQUENCE DESCRIPTION: SEQ ID NO:37:

Gln Leu Gly Val Met
    1               5

(2) INFORMATION FOR SEQ ID NO:38:

(i) SEQUENCE CHARACTERISTICS:
                (A) LENGTH: 6 amino acids
                (B) TYPE: amino acid
                (C) STRANDEDNESS:
                (D) TOPOLOGY: linear (ii) MOLECULE TYPE: peptide (v) FRAGMENT TYPE: internal (xi) SEQUENCE DESCRIPTION: SEQ ID NO:38:

Gln Leu Gly Val Met Gln
    1               5

(2) INFORMATION FOR SEQ ID NO:39:

(i) SEQUENCE CHARACTERISTICS:
                (A) LENGTH: 5 amino acids
                (B) TYPE: amino acid
                (C) STRANDEDNESS:
                (D) TOPOLOGY: linear (ii) MOLECULE TYPE: peptide (v) FRAGMENT TYPE: internal (xi) SEQUENCE DESCRIPTION: SEQ ID NO:39:

Ala Ala Ala Ser Leu
    1               5

(2) INFORMATION FOR SEQ ID NO:40:

(i) SEQUENCE CHARACTERISTICS:
                (A) LENGTH: 6 amino acids
                (B) TYPE: amino acid
                (C) STRANDEDNESS:
                (D) TOPOLOGY: linear (ii) MOLECULE TYPE: peptide (v) FRAGMENT TYPE: internal

```
        (xi) SEQUENCE DESCRIPTION: SEQ ID NO:40:

Ala Ala Ala Ser Leu Lys
1               5

(2) INFORMATION FOR SEQ ID NO:41:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:41:

Val Ala Val Ser Ala
1               5

(2) INFORMATION FOR SEQ ID NO:42:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:42:

Val Ala Val Ser Ala Lys
1               5

(2) INFORMATION FOR SEQ ID NO:43:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:43:

Leu Ala Ala Asn Leu
1               5

(2) INFORMATION FOR SEQ ID NO:44:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (v) FRAGMENT TYPE: internal (xi) SEQUENCE DESCRIPTION: SEQ ID NO:44:

Leu Ala Ala Asn Leu Arg
1               5
```

```
(2) INFORMATION FOR SEQ ID NO:45:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:45:

Gly Pro Gln Gly Ile
1               5

(2) INFORMATION FOR SEQ ID NO:46:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:46:

Gly Pro Gln Gly Ile Ala
1               5

(2) INFORMATION FOR SEQ ID NO:47:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:47:

Gly Pro Gln Gly Leu
1               5

(2) INFORMATION FOR SEQ ID NO:48:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:48:

Gly Pro Gln Gly Leu Leu
1               5

(2) INFORMATION FOR SEQ ID NO:49:

(i) SEQUENCE CHARACTERISTICS:
        (A) LENGTH: 5 amino acids
        (B) TYPE: amino acid
        (C) STRANDEDNESS:
        (D) TOPOLOGY: linear
```

```
        (ii) MOLECULE TYPE: peptide (v) FRAGMENT TYPE: internal (xi) SEQUENCE DESCRIPTION: SEQ ID NO:49:

Gly Pro Gln Gly Leu
1               5

(2) INFORMATION FOR SEQ ID NO:50:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO:50:

Gly Pro Gln Gly Leu Ala
1               5

(2) INFORMATION FOR SEQ ID NO:51:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO:51:

Gly Ile Ala Gly Ile
1               5

(2) INFORMATION FOR SEQ ID NO:52:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (v) FRAGMENT TYPE: internal (xi) SEQUENCE DESCRIPTION: SEQ ID NO:52:

Gly Ile Ala Gly Ile Thr
1               5

(2) INFORMATION FOR SEQ ID NO:53:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (v) FRAGMENT TYPE: internal
```

(xi) SEQUENCE DESCRIPTION: SEQ ID NO:53:

Gly Leu Pro Gly Ile
1               5

(2) INFORMATION FOR SEQ ID NO:54:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:54:

Gly Leu Pro Gly Ile Gly
1               5

(2) INFORMATION FOR SEQ ID NO:55:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:55:

Gly Phe Pro Gly Ile
1               5

(2) INFORMATION FOR SEQ ID NO:56:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:56:

Gly Phe Pro Gly Ile Gly
1               5

(2) INFORMATION FOR SEQ ID NO:57:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:57:

Gly Pro Ala Gly Ile
1               5

```
(2) INFORMATION FOR SEQ ID NO:58:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:58:

Gly Pro Ala Gly Ile Ser
1               5

(2) INFORMATION FOR SEQ ID NO:59:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:59:

Gly Pro Ala Gly Ile
1               5

(2) INFORMATION FOR SEQ ID NO:60:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:60:

Gly Pro Ala Gly Ile Ala
1               5

(2) INFORMATION FOR SEQ ID NO:61:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:61:

Ser Gly Thr Glu Ile
1               5

(2) INFORMATION FOR SEQ ID NO:62:

(i) SEQUENCE CHARACTERISTICS:
        (A) LENGTH: 6 amino acids
        (B) TYPE: amino acid
        (C) STRANDEDNESS:
        (D) TOPOLOGY: linear
```

-continued

```
    (ii) MOLECULE TYPE: peptide (v) FRAGMENT TYPE: internal (xi) SEQUENCE DESCRIPTION: SEQ ID NO:62:

Ser Gly Thr Glu Ile Val
1               5
```

NUCLEIC ACID CONSTRUCT FOR EXPRESSING ACTIVE SUBSTANCES WHICH CAN BE ACTIVATED BY PROTEASES, AND PREPARATION AND USE

BACKGROUND OF THE INVENTION

The present invention relates to a nucleic acid construct for expressing active substances which can be activated by proteases and to its preparation and use.

Like inflamed areas, tumors are distinguished from the surrounding normal tissue by a substantial increase in the formation and secretion of proteases [Schmitt et al., Fibrinol. 6, 3 (1992), Cottam et al., Int. J. Oncol. 2, 861 (1993), Tryggvason et al., Breast Cancer Res. And Treatm. 24, 209 (1993), Leto et al., Anticancer Res. 12, 235 (1992), Hart, Fibrinol. 6, 11 (1992), Albini et al., J. Natl. Cancer Inst. 83, 735 (1991)]. Examples of these proteases are plasminogen activators, cathepsins and matrix metalloproteinases.

An essential function of these tumor proteases is to dissolve the extracellular matrix to allow the tumor cells to invade, and grow in an infiltrative manner in, normal tissue. At the same time, these proteases protect the tumor from the defence mechanisms of the body insofar as the active compounds which are required for defence are cleaved, and thereby inactivated, by the proteases which are formed by the tumor. Thus, for example, antibodies, cytokines and growth factors, complement factors, coagulation factors and mediators are inactivated by tumor proteases.

In the past, the aim was, therefore, to inhibit the infiltrative growth and metastatic growth of tumors, and inactivation of the defence mechanisms of the body, by inhibiting the tumor cell proteases [Hocman, Int. J. Biochem. 24, 1365 (1992), Troll et al., JNCI 73, 1245 (1984), Ray et al., Eur. Respir. 7, 2062 (1994), Koop et al., Cancer Res. 54, 4791 (1994), Chiriri et al., Int. J. Cancer 58, 460 (1994), Denhardt et al., 59, 329 (1993), Melchiori et al., Cancer Res. 52, 2353 (1992)]. However, particularly for stoichiometric and pharmacokinetic reasons, little success has previously been achieved in inhibiting tumor cell proteases.

An attempt was therefore made to use the tumor cell proteases to activate bacterial toxins such as *Staphylococcus aureus* α-hemolysin [Panchal et al., Nature Biotechn. 14, 852 (1996)]. For this, an amino acid sequence (SEQ ID NO:1), i.e. XX-Arg-X, was inserted into positions 129 to 132 of the α-hemolysin and in this way inactive mutants were produced which are only cleaved, and thereby activated, by tumor proteases such as cathepsin B.

Based on these results, proimmunolysins were proposed [Panchal et al., Nature Biotechn. 14, 852 (1996)], which proimmunolysins comprise an antibody which is coupled to a *Staphylococcus aureus* α-hemolysin which can be activated by tumor proteases or to a sea anemone equinatoxin II, with the antibody determining the target cell specificity of the coupling product.

However, the proposed concept suffers from the following disadvantages in relation to its use in tumor therapy:

In the first place, the authors chose xenogeneic nonendogenous lysins and/or toxins which are immunogenic for the host organism (for example, patients) and as a result induce an immune reaction in the host organism, which immune reaction neutralizes and inactivates the antibody/ toxin conjugate. In the second place, it is known [Sedlacek et al., Antibodies as Carriers of Cytotoxicity, Contrib. to Oncol. 43, Karger Verlag, Munich, 1992] that, due to their molecular size and to the rheological conditions at the tumor, tumor-specific antibodies and immunotoxins only accrue in very small quantities (0.01–0.001% of the given antibody or immunotoxin/g of tumor) at the tumor and only penetrate the tumor to an incomplete extent so that it is either not possible to destroy all the tumor cells or only possible to destroy a small portion of the cells of a tumor. Then again, the extent to which tumor antigens, against which the antibody is directed, are expressed usually differs between the individual tumor cells, and the variable, antigen-negative tumor cells readily evade the attack by the antibodies or the immunotoxins. In addition to this, antigens which are secreted by the tumor cells neutralize the antibodies at the periphery of the tumor (Sedlacek et al., Monoclonal Antibodies in Tumor Therapy, Contrib. to Oncol., Karger Verlag, 1988).

Consequently, there is still a great need for a target cell-specific therapy for tumors and inflammations.

SUMMARY OF THE INVENTION

An object of the present invention is therefore to provide an active compound against tumors and inflammations, which active compound does not exhibit said disadvantages. The present invention therefore relates to a novel technique which uses the secretion of enzymes in tumors or areas of inflammation to achieve the local release of active compounds whose inactive precursors are expressed in tumor cells, tumor-associated cells or inflammatory cells.

One part of the subject-matter of the present invention is therefore a nucleic acid construct for expressing an active substance which is activated by an enzyme which is released from mammalian cells, which nucleic acid construct comprises the following components:

a) at least one promoter element, b) at least one DNA sequence which encodes an active compound (protein B), c) at least one DNA sequence which encodes an amino acid sequence (part structure C) which can be cleaved specifically by an enzyme which is released from a mammalian cell, and d) at least one DNA sequence which encodes a peptide or protein (part structure D) which is bound to the active compound (protein B) by way of the cleavable amino acid sequence (part structure C) and inhibits the activity of the active compound (protein B).

Further objects of the instant invention are described as follows:

1. A nucleic acid construct for expressing an active substance which is activated by an enzyme which is released from mammalian cells, wherein the construct comprises the following nucleic acid sequences in the following order:

a) at least one promoter element operably linked to;

b) at least one nucleic acid sequence which encodes an active compound, wherein the active compound is endogenous to mammals, operably linked to;

c) at least one nucleic acid sequence which encodes an amino acid sequence cleavable specifically by an enzyme which is released from a mammalian cell, operably linked to;

d) at least one DNA sequence which encodes a polypeptide which is bound to the active compound by the cleavable amino acid sequence and inhibits the activity of the active compound, and wherein the nucleic acid component c) does not naturally occur as operably linking the nucleic acid sequence b) to the nucleic acid d).

2. A nucleic acid construct as described in 1, wherein the enzyme is a protease.

3. A nucleic acid construct as described in 1, wherein the enzyme is a prostate specific antigen, a plasminogen activator, a cathepsin or a matrix metalloproteinase.

4. A nucleic acid construct as described in 1, wherein the mammalian cells are tumor cells, leukemia cells, endothelial cells, macrophages, lymphocytes, muscle cells, epithelial cells, glia cells, synovial cells or virus-infected cells.

5. A nucleic acid construct as described in 1, wherein the nucleic acid construct further comprises a nucleic acid sequence operably linked to the construct of 1, wherein the nucleic acid sequence encodes a ligand which binds the active compound to a target structure.

6. A nucleic acid construct as described in 1, wherein the nucleic acid sequences b) and d) of 1 encode parts of a natural precursor of a protein active compound, wherein the nucleic acid sequence encoding the cleavage sequence naturally occurring between the nucleic acid sequences b) and d) has been replaced by the nucleic acid sequence c), which does not naturally occur between the nucleic acid sequences b) and d).

7. A nucleic acid construct as described in 1, wherein the polypeptide encoded by the nucleic acid sequence d) is part of a natural precursor of a protein active compound.

8. A nucleic acid construct as described in 1, wherein the construct is operably inserted into a plasmid or a viral vector.

9. A nucleic acid construct as described in 1, wherein the nucleic acid sequence a) is a promoter sequence which can be activated nonspecifically, cell-specifically, virus-specifically, metabolically, cell cycle-specifically or by tetracycline.

10. A nucleic acid construct as described in 1, wherein the nucleic acid sequence a) comprises at least two identical or two different promoter sequences.

11. A nucleic acid construct as described 9, wherein the nucleic acid sequence a) is activated in endothelial cells, in cells adjoining activated endothelial cells, in muscle cells, in leukemia cells, in tumor cells, in glia cells, in lymphocytes, in macrophages or in synovial cells.

12. A nucleic acid construct as described in 1, wherein the active compound activates or inhibits a biological activation cascade or is an active component of this cascade, or activates or inhibits the coagulation system, activates fibrinolysis, activates the complement system or activates the kinin system, or is an enzyme which converts the inactive precursor of a pharmacological substance into the active substance, or which itself is a pharmacologically active substance.

13. A nucleic acid construct as described in 12, wherein the active compound is a coagulation factor which is selected from the group consisting of thrombin, factor Va, factor VIIa, factor IXa, factor Xa, TF coagulation-active fragments or factor XIIa; thrombin which is mutated in the region of the Arg-Thr cleavage site (amino acid position 327/328); a fibrinolytic protein which is selected from urokinase, tPA or functional hybrids thereof; a complement factor which is selected from CVF, C3b or functional cleavage products thereof; an antithrombotic protein which is selected from protein C, C-1S inhibitor, α1-antitrypsin, hirudin, AT-III, TFPI, PAI-1, PAI-2 or PAI-3; a kallikrein; a cytostatic, cytotoxic or inflammation-eliciting protein; an antiangiogenic protein; an immunomodulatory protein; an antiinflammatory protein; a protein which relieves damage to the nervous system; a protein which inhibits or neutralizes the neurotoxic effect of TNFα; an angiogenesis-stimulating protein; a hypotensive protein; an antiviral protein; a cytokine; an interferon; a tumor necrosis factor; oncostatin M or LIF; a cytokine receptor; the moiety of a cytokine receptor which is external to the cell; a cytokine antagonist; a growth factor; a growth factor receptor; the moiety of a growth factor receptor which is external to the cell; a chemokine; angiostatin; platelet factor 4; TIMP-1, TIMP-2 or TIMP-3; a nitroreductase; a β-glucuronidase; a carboxypeptidase; a β-lactamase; a cytosine deaminase; a catalase; a peroxidase; a phosphatase; an oxidase; kallikrein or an endothelial cell nitric oxide synthase.

14. A nucleic acid construct as described in 1, which further comprises a nucleic acid sequence b') which encodes a ligand which binds to a cell membrane receptor, a cell membrane antigen, a cell membrane-located adhesion molecule, or to the extracellular matrix or component thereof.

15. A nucleic acid construct as described in 14, wherein the ligand is an antibody or an antibody fragment which binds specifically to a cell membrane antigen or to an antigen on the extracellular matrix, or is a polypeptide which binds to receptor on the cell membrane wherein the polypeptide is a growth factor, a cytokine, an interferon, a tumor necrosis factor, a chemokine, a receptor-binding part sequence of these ligands, a peptide hormone, angiotensin, kinin, folic acid, an adhesion molecule or the part sequence of the adhesion molecule which binds to the corresponding adhesion molecule or to the extracellular matrix, an extracellular moiety of an Fc receptor, a glycoprotein of a virus, a part sequence of the glycoprotein which binds to these cells, the transmembrane domain of a receptor or of a viral glycoprotein, or a glycophospholipid anchor.

16. A nucleic acid construct as described in 14, wherein the ligand binds to activated or proliferating endothelial cells, to tumor cells, to muscle cells, preferably smooth muscle cells, to fibroblasts, to macrophages, to lymphocytes, to liver cells, to kidney cells, to synovial cells, to inflammatory cells, to virus-infected cells, to bronchial epithelial cells, to glia cells or to leukemia cells.

17. A nucleic acid construct as described in 14, wherein the construct comprises at least two identical or different nucleic acid sequences b)c)d) or b')b)c)d), which nucleic acid sequences are linked to each other by way of an internal ribosomal entry site.

18. A process for preparing a nucleic acid construct according to 1, which comprises operably linking the nucleic acid sequences of 1.

19. A method for the treatment or prophylaxis of tumors, leukemias, allergies, autoimmune diseases, infections, inflammations, transplant rejection reactions, thromboses, blood vessel occlusions, blood coagulation, blood circulation disturbances, injuries to tissues, or damage to the nervous system, comprising administering to a mammal an effective amount of a polypeptide expressed by the nucleic acid construct of 1.

20. A method for preparing a recombinantly altered cell, comprising transducing a suitable cell with the nucleic acid construct of 1.

21. A method for preparing a polypeptide which is encoded by the nucleic acid construct of 1, comprising transducing a suitable cell with the construct, expressing the polypeptide in the cell, and isolating the expressed polypeptide.

22. The method of 20, wherein the cell is an endothelial cell, a lymphocyte, a macrophage, a glia cell, a fibroblast, a liver cell, a kidney cell, a muscle cell, a cell of the bone or cartilage tissue, a synovial cell, a peritoneal cell, a skin cell, an epithelial cell, a leukemia cell or a tumor cell.

23. The method of 21, wherein the cell is an endothelial cell, a lymphocyte, a macrophage, a glia cell, a fibroblast, a liver cell, a kidney cell, a muscle cell, a cell of the bone or cartilage tissue, a synovial cell, a peritoneal cell, a skin cell, an epithelial cell, a leukemia cell or a tumor cell.

24. A cell transduced with the nucleic acid construct of 1.

25. A protein encoded by the nucleic acid construct of 1.

The term "endogenous to mammals" as used to describe the active compound of the instant invention denotes a polypeptide that is naturally expressed in mammals or a derivative thereof as discussed herein.

The term "does not naturally occur" as used to describe the linking nucleic acid component c) denotes that the described component c) of the instant invention is not found in nature as operably linking components b) and d).

BRIEF DESCRIPTION OF THE DRAWINGS

FIG. 3 is diagrammatic representation of a nucleic acid construct for PSA-activatable factor X.

DETAILED DESCRIPTION OF THE PREFERRED EMBODIMENTS

Figure 1:
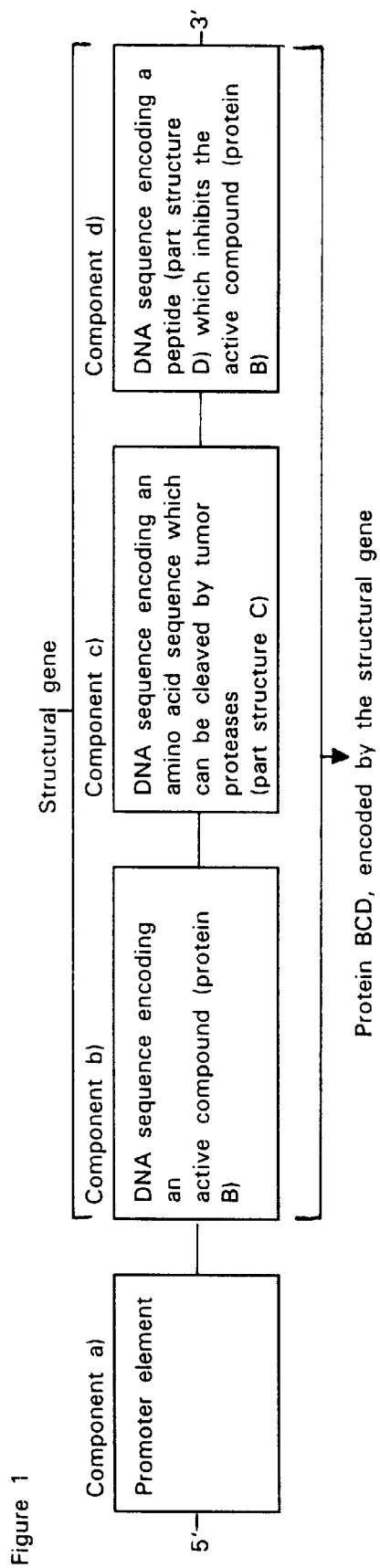
FIG. 1 is a diagrammatic representation of a novel nucleic acid construct comprising components a), b), c) and d)

In their simplest form, the individual components can be arranged, for example, as shown in FIG. 1. In this case, expression of a protein BCD, encoded by components b), c) and d), is induced by activating the promoter sequence [component a)]. The amino acid sequence C of the expression product is then cleaved by cellular enzymes, e.g. proteases, as a result of which protein B, which constitutes the active compound, is released. Within the meaning of the present invention, proteases or enzymes are to be understood as being one or more proteases or enzymes.

In another embodiment, said enzyme is a protease, in particular a plasminogen activator, a cathepsin or a matrix metalloproteinase. Said mammalian cells are preferably tumor cells, leukemia cells, endothelial cells, macrophages, lymphocytes, muscle cells, epithelial cells, glia cells, synovial cells or virus-infected cells.

Enzymes are preferably released, in an organism, by tumors and tumor cells and also by cells which are involved in an inflammatory process [Barrett et al., Mammalian Proteases, Academic Press, London 1980; Sedlacek and M öroy, Immune Reactions, Springer Verlag, 1995)].

According to the present invention, component c) is consequently selected such that the expressed protein, e.g. BCD, is preferably cleaved, in its part structure C, by proteases which are formed in tumors or secreted by tumor cells or inflammatory cells. Examples of these proteases are plasminogen activators, such as plasminogen activator of the urokinase type or tissue plasminogen activator; cathepsins, such as cathepsin B, cathepsin D, cathepsin L, cathepsin E or cathepsin H, or their precursors (procathepsins); matrix metalloproteinases (MMP), such as collagenases, for example of groups I, II, III, IV or V; stromelysin 1, stromelysin 2 or stromelysin 3; metrilysins; gelatinases, such as gelatinase A (MMP 2), and progelatinase B (MMP 9) and progelatinase A [Pappot et al., Lung Cancer 12, 1 (1995), Schmitt et al., Fibronolysis 614, 3 (1992), Monsky et al., Cancer Biol. 4, 251 (1993), Rochefort et al., Medicine/ Sciences 7, 30 (1991), Kao et al., 46, 1349 (1986), Fridman et al., Cancer Res. 55, 2548 (1995), Ray et al., Eur. Respir. J. 7, 2062 (1994), Cottam et al., Int. J. Oncol. 2, 861 (1993), Tryggvason et al., Breast Cancer Res. and Treatm. 24, 209 (1993)]; tumor cell surface proteases [surface-expressed proteases=seprase; Monsky et al., Cancer Res. 54, 5702 (1994)]; elastase [Kao et al., Cancer Res. 46, 1355 (1986)]; prostate-specific antigen [Lundwall, Biochem. Biophys. Res. Commun. 161, 1151 (1989), Riegman et al., Biochem. Biophys. Res. Commun. 159, 95 (1989)] or pancreatic trypsinogens [Miszuk-Jamska et al., FEBS Lett. 294, 175 (1991)].

Figure 2:
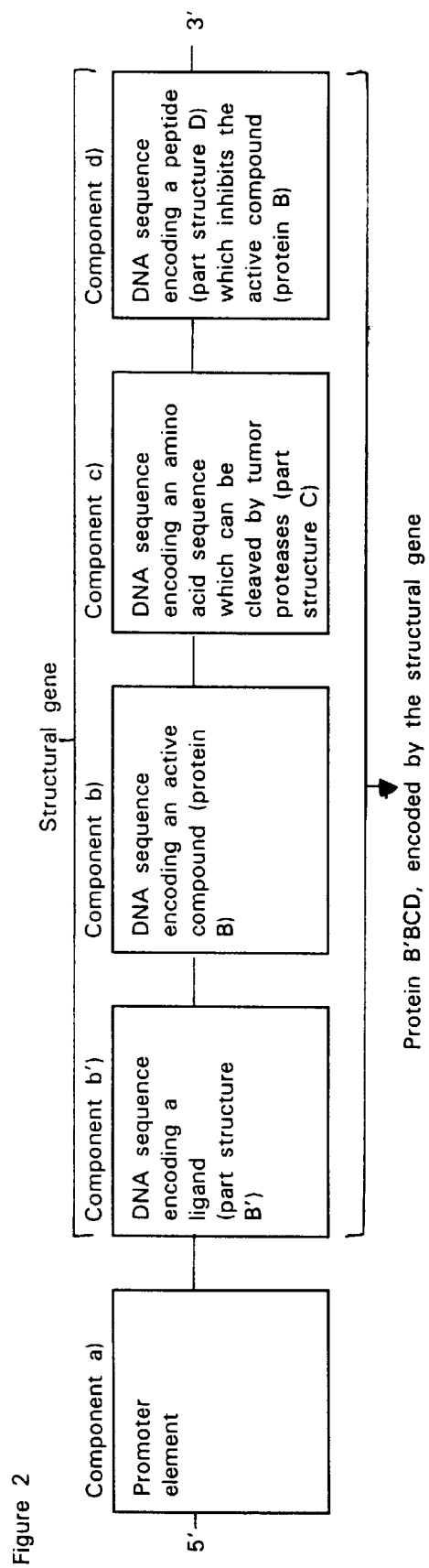
FIG. 2 is a diagrammatic representation of a novel nucleic acid construct which has been enlarged by adding component b')

In accordance with another embodiment of the present invention, the nucleotide sequence for component b) can be extended by the addition of a component b'). This component b') encodes a ligand (part structure B') which can bind the active compound to a target structure. Component b') is, for example, arranged as shown in FIG. 2. Expression of the nucleic acid construct corresponding to FIG. 2 results in a protein, i.e. B'BCD, which binds to a target structure by way of the ligand (part structure B'). The part structure C is then cleaved by an enzyme, for example, cellular proteases, thereby releasing the active compound, i.e. protein B'B.

In a particular embodiment, said protein B and the part structure D are parts of the natural precursors of protein active compounds, with the natural cleavage sequence, which connects the part structures B and D, having been replaced by the part structure C; in particular, said part structure D is the part structure of a natural precursor of a protein active compound.

The novel nucleic acid constructs are preferably composed of DNA. The term "nucleic acid constructs" is understood to mean artificial nucleic acid structures which can be transcribed in the target cells. They are preferably inserted into a vector, with plasmid vectors or viral vectors being particularly preferred.

Depending on the choice of the promoter element [component a)], the novel nucleic acid constructs express a structural gene [components b)+c)+d) or b')+b)+c)+d)] either nonspecifically, cell-specifically, virus-specifically, under particular metabolic conditions, cell cycle-specifically or in the presence of tetracycline. At least two identical or different promoter elements can also be combined together for the purpose of modifying the expression of the structural gene depending on the choice of these promoter elements. Component a) is preferably activated in endothelial cells, in cells adjoining activated endothelial cells, in muscle cells, in leukemia cells, in tumor cells, in glia cells, in lymphocytes, in macrophages and/or in synovial cells.

The part structure B (protein B) of the protein encoded by the novel structural gene constitutes the actual novel active compound which is released or activated by cleavage of the part structure C and thereby converted from the inhibited state, e.g. as protein BCD or as protein B'BCD, into the active state, e.g. as protein B or as protein B'B.

According to the invention, this active compound can be an enzyme which activates or inhibits a biological activation cascade and/or is an active component of this cascade. Examples of biological activation cascades of this nature are the coagulation system, which can be activated or inhibited, fibrinolysis, which is preferably activated, the complement system, which is likewise preferably activated, or the kinin system, which is also preferably activated. The active compound can also be an enzyme which converts the inactive precursor of a pharmacological substance into the active substance or which itself is a pharmacologically active substance. Particular preference is given to an active compound (protein B) which is a coagulation factor which is selected from thrombin, factor Va, factor VIIa, factor IXa, factor Xa, TF coagulation-active fragments or factor XIIa; thrombin which is mutated in the region of the Arg-Thr cleavage site (amino acid position 327/328); a fibrinolytic protein which is selected from urokinase, tPA or functional hybrids thereof; a complement factor which is selected from CVF, C3b or functional cleavage products thereof; an antithrombotic protein which is selected from protein C, C-1S inhibitor, α1-antitrypsin, hirudin, AT-III, TFPI, PAI-1, PAI-2 or PAI-3; a kallikrein; a cytostatic, cytotoxic or inflammation-eliciting protein; an antiangiogenic protein; an immunomodulatory protein; an antiinflammatory protein; a protein which relieves damage to the nervous system; a protein which inhibits or neutralizes the neurotoxic effect of TNFα; an angiogenesis-stimulating protein; a hypotensive protein; an antiviral protein; a cytokine; an interferon; a tumor necrosis factor; oncostatin M or LIF; a cytokine receptor; the moiety of a cytokine receptor which is external to the cell; a cytokine antagonist; a growth factor; a growth factor receptor; the moiety of a growth factor receptor which is external to the cell; a chemokine; angiostatin; platelet factor 4; TIMP 1, TIMP 2 or TIMP 3; a nitroreductase; a β-glucuronidase; a carboxypeptidase; a β-lactamase; a cytosine deaminase; a catalase; a peroxidase; a phosphatase; an oxidase; kallikrein or an endothelial cell nitric oxide synthase.

The part structure B' of the protein encoded by the novel structural gene constitutes the novel ligand for binding the active compound (protein B) to a target structure. A preferred target structure is the surface of cells, preferably a cell membrane receptor, a cell membrane antigen, a cell membrane-located adhesion molecule, or the extracellular matrix, for example of endothelial cells, in particular of activated or proliferating endothelial cells, tumor cells, muscle cells, in particular smooth muscle cells, fibroblasts, macrophages, lymphocytes, liver cells, kidney cells, synovial cells, inflammatory cells, virus-infected cells, bronchial epithelial cells, glia cells, leukemia cells or cells of other tissues and organs. A particularly preferred target structure is the surface of activated and/or proliferating endothelial cells.

Another preferred target structure is constituted by components of the extracellular matrix, for example collagens [Prockop et al., Annu. Rev. Biochem. 64, 403 (1995), Wetzels et al., Am. J. Pathol. 139, 451 (1991)]; ficolin [Ichijo et al., J. Biol. Chem. 268, 14505 (1993)]; sialoprotein [Bellahcene et al., Cancer Res. 54, 2823 (1994)]; laminin [von der Mark et al., Biochem. Biophys. Acta 823, 147 (1985); Hunt. Expl. Cell Biol. 57, 165 (1989)]; proteoglycans [Schmidtchen et al., Biomed. Chromatography 7, 48 (1993)] or tenascin [Oyama et al., Cancer Res. 51, 4876 (1991); Herlyn et al., Cancer Res. 51, 4853 (1991)].

The novel ligand (part structure B') can, for example, be an antibody or an antibody fragment, such as the epitope-binding moiety of an antibody, Fab, Fv, single-chain Fv or Fc, which binds specifically to a cell membrane antigen or to an antigen on the extracellular matrix, or another peptide or protein which binds to a receptor on the relevant cell membrane. These include, for example, growth factors, cytokines, interferons, tumor necrosis factor, chemokines, their receptor-binding part sequences, peptide hormones, angiotensin, kinin or folic acid. The ligand can also be an adhesion molecule or its adhesion sequence which binds to a corresponding molecule on the cell membrane or on the extracellular matrix, or the target cell-binding moiety, an extracellular moiety of an Fc receptor, a target cell-binding glycoprotein of a virus which has a tropism for selected cells, or a part sequence of the glycoprotein which binds to these cells, or a peptide by whose help the active compound is anchored in the cell membrane of the cell which is expressing it. Examples of these anchoring peptides are the transmembrane domains of receptors or virus proteins or glycophospholipid anchors.

Component d) encodes a peptide (part structure D) which is bonded to protein B or protein B'B by way of part structure C and thereby inhibits the activity of protein B. Component d) can be any arbitrary nucleic acid sequence. Preferably, however, it is composed of nucleic acid sequences which encode endogenous peptides or proteins, in order to avoid or decrease the danger of an immune reaction. In another preferred embodiment, components b) and d) of the novel structural gene encode endogenous proteins or peptides.

A considerable number of protein active compounds occur in nature in the form of inactive precursors (protein BSD). A precursor of this type is activated by enzymes cleaving this precursor into a part structure which constitutes the actual protein active compound (protein B) and into an inactive part structure (part structure D). This precursor is cleaved at least one defined amino acid sequence, i.e. the so-called cleavage sequence (part structure S).

It is a particular part of the subject-matter of this invention that this cleavage sequence (part structure S) which occurs naturally in precursors of protein active compounds is replaced by the part structure C. This replacement is effected by the sequence encoding the part structure S being replaced by component c), encoding part structure C, in the nucleic acid sequence which encodes the natural precursor (protein BSD). After components a) and, where appropriate, b') have been added on, a novel nucleic acid construct is produced which comprises, for example, components a)b')b)c)d) or a)b)c)d), the part structure C of whose expression product, i.e. protein B'BCD or BCD, respectively, is cleaved by proteases which are formed in tumors or secreted by tumor cells or inflammatory cells, such that the active compound, i.e. protein B'B or B, can be formed.

In another embodiment, the novel construct comprises at least two identical or different components b)c)d) and/or b')b)c)d), which components are linked to each other by way of a so-called internal ribosomal entry site (IRES).

Having been inserted into a nonviral vector or viral vector, the novel nucleic acid construct is generally, for the prophylaxis and/or therapy of disorders, administered locally or injected into the blood circulation. These disorders particularly include tumor diseases and inflammations. Such inflammations can be triggered, for example, by physicochemical damage, by an infection or by an immune reaction against endogenous or foreign tissue.

The present invention furthermore relates, therefore, to the use of a novel nucleic acid construct for preparing a drug for local or systemic administration for the prophylaxis and/or therapy of tumors, leukemias, allergies, autoimmune diseases, infections, inflammations, transplant rejection reactions, thromboses, blood vessel occlusions, blood coagulation and blood circulation disturbances, and injuries to tissues and/or damage to the nervous system.

The choice of the components of the novel nucleic acid construct depends on the disease which is to be treated by administering the nucleic acid construct and can be made as follows:

Promoter Sequences [Component a)]

According to the present invention, particular preference is given, on the one hand, to promoter sequences

[component a)] which are promoters and activator sequences which can be activated in an unrestricted manner, such as the promoter of RNA polymerase III, the promoter of RNA polymerase II, etc., the CMV promoter and CMV enhancer, or the SV40 promoter, and, on the other hand, to viral promoter and activator sequences, such as HBV, HCV, HSV, HPV, EBV, HTLV or HIV.

For example, in the case of the HIV promoter, the entire LTR sequence, including the TAR sequence [positions≦−453 to ≧−80, Rosen et al., Cell 41, 813 (1985)] can be used as a virus-specific promoter.

Metabolically activatable promoter and enhancer sequences, such as the hypoxia-inducible enhancer, promoters which can be activated in a cell cycle-specific manner, such as the promoters of the cdc25C gene, the cyclin A gene, the cdc2 gene, the Bmyb gene, the DHFR gene or the E2F-1 gene, or tetracyline-activatable promoters, such as the tetracycline operator in combination with an appropriate repressor, are also particularly preferred as component a).

According to the present invention, nucleotide sequences which, after binding transcription factors, activate the transcription of a structural gene which adjoins them at the 3' end are also to be used as promoter sequences.

In addition, promoters which can be activated in a cell-specific manner are particularly preferred as component a). These promoters preferably include promoters or activator sequences composed of promoters or enhancers from those genes which preferably encode proteins in selected cells. For example, promoters for the following proteins are preferably to be used in the following cells:

Promoter and activator sequences which are activated in endothelial cells, such as brain-specific, endothelial glucose-I transporter, endoglin, VEGF receptor 2 (flt-1), VEGF receptor 2 (flk-1, KDR), tiel-1 or tiel-2, B61 receptor (Eck receptor), B61, endothelin especially endothelin B and endothelin 1, endothelin receptors, in particular the endothelin B receptor, mannose 6-phosphate receptors, von Willebrand factor, IL-1α, IL-1β, IL-1 receptor, vascular cell adhesion molecule (VCAM 1) or synthetic activator sequences.

As an alternative to natural, endothelial cell-specific promoters, use can also be made of synthetic activator sequences which are composed of oligomerized binding sites for transcription factors which are preferentially or selectively active in endothelial cells. An example is transcription factor GATA 2, whose binding site in the endothelin 1 gene is 5'-TTATCT-3' [Lee et al., Biol. Chem. 266, 16188 (1991), Dormann et al., J. Biol. Chem. 267, 1279 (1992) and Wilson et al., Mol. Cell. Biol. 10, 4854 (1990)].

Promoters or activator sequences which are activated in cells in the vicinity of activated endothelial cells, in particular in smooth muscle cells, are present, for example, in the VEGF gene. The gene-regulatory sequences for the VEGF gene are the 5'-flanking region, the 3'-flanking region, the c-Src gene or the v-Src gene.

Steroid hormone receptors and their promoter elements, in particular the mouse mammary tumor virus promoter, or promoter elements of the gene encoding tropomyosin, α-actin, α-myosin, the receptor for PDGF, the receptor for FGF, MRF-4, phosphofructokinase A, phosphoglycerate mutase, troponin C, myogens, receptors for endothelin A, desmin or separate "artificial" promoters, are also suitable. Promoter elements to which the factors of the helix-loop-helix (HLH) family (MyoD, Myf 5, myogens and MRF4 [review in Olson and Klein, Genes Dev. 8, 1 (1994)]) can bind, as muscle-specific transcription factors, are likewise suitable. The muscle-specific transcription factors also include the zinc finger protein GATA-4 (Arceci et al., Mol. Cell Biol. 13, 2235 (1993), Ip et al., Mol. Cell Biol. 14, 7517 (1994)] and the groups of the MEF transcription factors [Yu et al., Gene Dev. 6, 1783 (1992)].

The HLH proteins, and also GATA 4, exhibit a similar muscle-specific transcription not only with promoters from muscle-specific genes but also in a heterologous context, that is with "artificial" promoters. Examples of such artificial promoters are multiple copies of the (DNA) binding site for muscle-specific HLH proteins, such as the E box (myo D), e.g. (SEQ ID NO:2) 4× AGCAGGTGTTGGGAGGC, [Weintraub et al., PNAS 87, 5623 (1990)] or multiple copies of the DNA binding site for GATA 4 of the α-myosin heavy chain gene, e.g. (SEQ ID NO:3) 5'-GGCCGATGGGCAG ATAGAGGGGGCCGATGGGCAGATAGAGG3' [Molkentin et al., Mol. Cell Biol. 14, 4947 (1994)].

Examples of promoters and activator sequences which are activated in leukemia cells are promoters for c-myc, HSP-70, bcl-1/cyclin D-1, bcl-2, IL-6, IL-10, TNFα, TNFβ, HOX-11, BCR-Abl, E2A-PBX-1 or PML-RATA.

Examples of promoters or activator sequences which are activated in tumor cells are promoter or activator sequences which interact with the transcription factors which are formed, or are active, in tumor cells. These preferred promoter or activator sequences include gene-regulatory sequences or elements from genes which encode proteins which are formed, in particular, in cancer cells or sarcoma cells. Thus, for example, the promoter of the N-CAM protein is used in the case of small-cell bronchial carcinomas, the promoter of the hepatitis growth factor receptor or of L-plastin is used in the case of ovarian carcinomas, and the promoter of L-plastin or of polymorphic epithelial mucin (PEM) is used in the case of pancreatic carcinomas.

Promoters and activator sequences which are activated in glia cells are, in particular, the gene-regulatory sequences or elements from genes which encode, for example, the following proteins: the Schwann cell-specific protein periaxin, glutamine synthetase, glia cell-specific protein (glial fibrillary acid protein=GFAP), the glia cell protein S100b, IL-6 (CNTF), 5-HT receptors, TNFα, IL-10, insulin-like growth factor receptor I and II or VEGF. The gene-regulatory sequences for the VEGF gene have already been listed above.

Examples of promoters and activator sequences which are activated in lymphocytes and/or macrophages are the promoter and activator sequences of the gene encoding cytokines, cytokine receptors and adhesion molecules, and receptors for the Fc fragment of antibodies. Examples of these are: IL-1 receptor, IL-1α, IL-1β, IL-2, IL-2 receptor, IL-3, IL-3 receptor (α subunit), IL-3 receptor (β subunit), IL-4, IL-4 receptor, IL-5, IL-6, IL-6 receptor, interferon regulatory factor 1 (IRF-1), (the promoter of IRF-1 is activated to the same extent by IL-6 as by IFNγ or IFNβ), IFNγ-responsive promoter, IL-7, IL-8, IL-10, IL-11, IFNγ, GM-CSF, GM-CSF receptor (α chain), IL-13, LIF, macrophage colony stimulating factor (M-CSF) receptor, type I and II macrophage scavenger receptors, MAC-1 (leukocyte function antigen), LFA-1α (leukocyte function antigen) or p150,95 (leukocyte function antigen).

Examples of promoter and activator sequences which are activated in synovial cells are the promoter sequences for matrix metalloproteinases (MMP), for example for: MMP-1 (interstitial collagenase), or MMP-3 (stromelysin/transin). These also include the promoter sequences for tissue inhibitors of metalloproteinases (TIMP), for example TIMP-1, TIMP-2 and TIMP-3.

According to the present invention, several of the promoter sequences which have been listed by way of example can be combined with each other in order to achieve the highest possible target cell specificity in the expression of the novel nucleic acid construct. Two identical promoters can also be combined. Several promoter sequences can be combined, for example, using chimeric promoters or hybrid promoters. A chimeric promoter is the combination of an upstream activator sequence, which can be activated cell-specifically, metabolically or virus-specifically, with a downstream promoter module which binds the transcription factors of the CDF and CHF families or the E2F and CHF families and can thereby inhibit activation of the upstream activator sequence in the G0 and G1 phases of the cell cycle (Lucibello et al., EMBO J. 14, 132 (1994)].

In the case of hybrid promoters, the TATA box of a promoter is, for example, mutated, with this mutation being compensated for by a corresponding mutation in the gene for a TATA-binding protein, and this TATA-binding protein being under the control of another promoter.

Nucleic Acid Sequence [Component b')], Which Encodes a Ligand (Part Structure B')

According to the present invention, the ligand is a substance which binds a membrane antigen to a receptor or to an adhesion molecule on the target cell or which is integrated in the cell membrane and/or binds to the extracellular matrix. Reviews of the important cytokines and growth factors and their receptors, adhesion molecules and extracellular matrix proteins are provided by Ayad et al., The Extracellular Matrix, Academic Press 1994; Callard et al., The Cytokine, Academic Press 1994; Pigott et al., The Adhesion Molecule, Academic Press 1994, and Barclay et al., The Leucocyte Antigen, Academic Press 1994.

Examples of substances which bind to receptors are growth factors, such as VEGF, PDGF, EGF, TGFα, TGFβ, KGF, SDGF, FGF, IGF, HGF, NGF, BDNF, neurotrophins, BMF, bombesin, M-CSF, thrombopoietin, erythropoietin, SCF, SDGF, oncostatin, PDEGF or endothelin-1, cytokines, such as IL-1, IL-2, IL-3, IL-4, IL-5, IL-6, IL-7, IL-8, IL-9, IL-10, IL-11, IL-12, IL-13, IL-14, IL-15, interferons α, β and γ, tumor necrosis factors TNFα and TNFβ, chemokines, such as RANTES, MCAF, MIP-1α or MIP-1β, NAP or β-thromboglobulin, peptide hormones, such as SRH, SIH or STH, MRH or MSH, PRH, PIH or prolactin, LH-RH, FSH-RH, LH/ICSH or FSH, TRH or TSH, CRH or ACTH, angiotensin, kinins, homologs or analogs thereof, or vitamins, such as folic acid.

According to the present invention, the ligand can also be an adhesion molecule, a part of an adhesion molecule or an analog of an adhesion molecule which binds to a corresponding adhesion molecule which is located in the cell membrane or to another specific binding structure for an adhesion molecule on the target cell or in the extracellular matrix.

Examples of such adhesion molecules which are capable of functioning as ligands are Lewis X (for GMP-140), S Lewis X (for ELAM-1), LFA-1 (for ICAM-1 and ICAM-2), MAC-1 (for ICAM-1), VLA-4 (for VCAM-1), PECAM (for PECAM), vitronectin (for the vitronectin receptor), GMP-140 (for Lewis X), S Lewis X (for ELAM-1), ICAM-1, ICAM-2 (for LFA-1 and MAC-1), VCAM-1 (for VLA-4), fibronectin (for VLA-4), laminin (for VLA-6), laminin (for VLA-1, VLA-2 and VLA-3), fibrinogen (for GPIIb-IIIa), B7 (for CD28), CD28 (for B7), CD40 (for CD40L) or CD40L (for CD40).

According to the present invention, the ligand can also be the extracellular moiety of an Fc receptor [Dougherty et al., Transfusion Science 17, 121 (1996)]. Furthermore, the ligand can also be an antibody molecule or the epitope-binding moiety of an antibody molecule. The murine monoclonal antibodies should preferably be employed in humanized form. The humanization is effected in the manner described by Winter et al. Nature 349, 293 (1991) and Hoogenbooms et al. Rev. Tr. Transfus. Hemobiol. 36, 19 (1993).

Recombinant antibody fragments are either prepared directly from existing hybridomas or are isolated from libraries of murine or human antibody fragments [Winter et al., Annu. Rev. Immunol. 12, 433 (1994)] using the phage-display technique [Smith, Science 228, 1315 (1985)]. The antibody fragments are then employed directly, at the genetic level, for further manipulations, e.g. for fusion with other proteins.

In order to prepare recombinant antibody fragments from hybridomas, the genetic information which encodes the antigen-binding domains (VH and VL) of the antibodies is obtained by isolating the mRNA, reverse-transcribing the RNA into cDNA and then amplifying the cDNA by means of the polymerase chain reaction [Saiki et al., Science 230, 1350 (1985)] and using oligonucleotides which are complementary to the 5' and 3' ends of the variable fragments (Orlandi et al., 1989). The VH and VL fragments are then cloned into bacterial expression vectors, for example in the form of Fv fragments [Skerra & Plückthun, Science 240, 1038 (1988)], single-chain Fv fragments (scFv) [Bird et al., Science 242, 423 (1988), Huston et al., PNAS-U.S.A. 85, 5879 (1988)] or as Fab fragments [Better et al., Science 240, 1041 (1988)].

The phage-display technique can also be used to isolate new antibody fragments directly from antibody libraries (immune libraries or naive libraries) of murine or human origin. In the phage-display of antibody fragments, the antigen-binding domains are cloned, as protein fusions with the coat protein g3P of filamentous bacteriophages, either into the phage genome [McCafferty et al., Nature 348, 552 (1990)] or into phagemid vectors [Breitling et al., Gene 104, 147 (1991)] in the form of scFv fragments [McCafferty et al., Nature 348, 552 (1990)] or as Fab fragments [Hoogenboom et al., Nucl. Acid Res. 19, 4133 (1991), Barbas et al., PNAS-U.S.A. 88, 7978 (1991)]. Antigen-binding phages are selected on antigen-loaded plastic vessels (panning) [Marks et al., J. Mol. Biol. 222, 581 (1991)], on antigen-conjugated, paramagnetic beads [Hawkins et al., J. Mol. Biol. 226, 889 (1992)] or by binding to cell surfaces [Marks et al., Bio/Technol. 11, 1145 (1993)].

Immune libraries are prepared by subjecting the variable antibody fragments from the B lymphocytes of immunized animals [Sastry et al., PNAS-U.S.A. 86, 5728 (1989), Ward et al., Nature 341, 544 (1989), Clackson et al., Nature 352, 624 (1991)] or patients [Mullinax et al., PNAS-U.S.A., 87, 8095 (1990), Barbas et al., PNAS-U.S.A., 88, 7978 (1991)] to PCR amplification. For this, use is made of combinations of oligonucleotides which are specific for murine [Orlandi et al., PNAS-U.S.A., 86, 3833 (1989), Sastry et al., PNAS-U.S.A., 86, 5728 (1989)] or human immunoglobulin genes [Larrick et al., BBRC 160, 1250 (1989)] or for the human immunoglobulin gene families [Marks et al., Eur. J. Immunol. 21, 985 (1991)].

Naive libraries can be prepared, for example, using non-immunized donors as the source of the immunoglobulin genes [Marks et al., J. Mol. Biol. 222, 581 (1991)]. Alternatively, immunoglobulin germ line genes can be used to prepare semisynthetic antibody repertoires, with the complementarity-determining region 3 of the variable fragments being amplified by PCR using degenerate primers [Hoogenboom & Winter, J. Mol. biol. 227, 381 (1992), Barbas et al., PNAS-U.S.A., 89, 4457 (1992), Nissim et al., EMBO J. 13, 692 (1994), Griffiths et al., EMBO J. 13, 3245 (1994)]. As compared with immune libraries, these so-called single-pot libraries have the advantage that antibody fragments against a large number of antigens can be isolated from one single library [Nissim et al., EMBO J, 13, 692 (1994)].

The phage-display technique can be used to increase the affinity of antibody fragments still further, with new libraries being prepared from already existing antibody fragments by random (Hawkins et al., J. Mol. Biol. 226, 889 (1992), Gram et al., PNAS-U.S.A., 89, 3576 (1992)], codon-based [Glaser et al., J. Immunol. 149, 3903 (1992)] or site-directed mutagenesis [Balint & Larrick, Gene 137, 109 (1993)], by shuffling the chains of individual domains with those of fragments from naive repertoires [Marks et al., Bio/Technol 10, 779 (1992)] or by using bacterial mutator strains [Low et al., J. Mol. Biol. 26, 359 (1996)], and antibody fragments having improved properties being isolated by reselecting under stringent conditions [Hawkins et al., J. Mol. Biol. 226, 889 (1992)]. In addition, murine antibody fragments can be humanized by a stepwise replacement of one of the variable domains with a human repertoire and then selecting with the original antigen (guided selection) [Jespers et al., Bio/Technol, 12, 889 (1994)]. Alternatively, murine antibodies are humanized by specifically replacing the hypervariable regions of human antibodies with the corresponding regions of the original murine antibody [Jones et al., Nature 321, 522 (1987)].

According to the present invention, the ligand can also be the nucleotide sequence encoding a coat protein, or a part of a coat protein, of viruses which specifically bind to selected cells by way of their coat protein.

The ligand can also be a peptide, with whose help the active compound (protein B) is anchored in the cell membrane of the expressing cells. These anchoring peptides include the transmembrane domains of cell membrane-located receptors or of virus proteins, such as the transmembrane sequence of human macrophage colony-stimulating factor [DNA position≦1485 to ≧1554; Cosman et al., Behring Inst. Mitt. 83, 15 (1988)] or the DNA sequence for the signal and transmembrane regions of human respiratory syncytial virus (RSV) glycoprotein G [amino acids 1 to 63 or their part sequences, amino acids 38 to 63; Vijaya et al., Mol. Cell Biol. 8, 1709 (1988); Lichtenstein et al., J. Gen. Virol. 77, 109 (1996)] or the DNA sequence for the signal and transmembrane region of influenza virus neuraminidase [amino acids 7 to 35 or the part sequence of amino acids 7 to 27, Brown et al., J. Virol. 62; 3824 (1988)].

However, the nucleotide sequence for a glycophospholipid anchor [review of glycophospholipid-anchored membrane proteins in Ferguson et al., (Ann. Rev. Biochem. 57, 285 (1988))] can also be inserted for the purpose of anchoring the active compound in the cell membrane of the transduced cells which form the active compound. Glycophospholipid anchors have been described, for example, for CEA [DNA position<893 to >1079; Berling et al., Cancer Res. 50 6534 (1990)], for N-CAM [Cunningham et al., Science 236, 799 (1987)] and for other membrane proteins such as Thy-1 [Clissold, Biochem. J. 281, 129 (1992)] or CD16 [Selvaray et al., Nature 333, 565 (1988)].

The choice of the ligand depends, first and foremost, on the target cell which is to be transduced with the nucleic acid construct. Ligands for activated endothelial cells are examples of this. Within the meaning of the invention, these ligands include antibodies or antibody fragments which are directed against membrane structures of endothelial cells, as have been described, for example, by Burrows et al. Pharmac. Ther. 64, 155 (1994), Hughes et al., Cancer Res. 49, 6214 (1989) and Maruyama et al., PNAS-U.S.A. 87, 5744 (1990). In particular, these antibodies include antibodies against actin, angiotensin II receptors, antibodies against receptors for growth factors such as VEGF, FGF, PDGF or BGF, and antibodies against adhesion molecules, for example against the vitronectin receptor or ICAM 3.

The ligands furthermore include all active compounds which bind to membrane structures or membrane receptors on endothelial cells. Examples of these are IL-1 or growth factors, or their fragments or part sequences thereof, which bind to receptors which are expressed in endothelial cells, for example PDGF, bFGF, VEGF or TGFβ [Pusztain et al., J. Pathol. 169, 191 (1993)].

The ligands furthermore include adhesion molecules which bind to activated and/or proliferating endothelial cells. Adhesion molecules of this nature, such as Slex, LFA-1, MAC-1, LECAM-1, VLA-4 or vitronectin, have already been described [Augustin-Voss et al., J. Cell Biol. 119, 483 (1992), Pauli et al., Cancer Metast. rev. 9, 175 (1990), Honn et al., Cancer Metast. Rev. 11, 353 (1992), Pigott et al., The Adhesion Molecule, Academic Press (1994)].

The ligands within the meaning of this invention also include, in particular, glycoproteins from the coats of viruses which have a tropism for endothelial cells. Examples of these viruses are filoviruses, such as Marburg virus with its coat proteins GP (glycoprotein) and sGP (second glycoprotein) or Ebola virus, in each case with its coat proteins GP and sG, cytomegalovirus, particularly with its gB protein, herpes simplex virus type I, HIV-1 virus, measles virus, Hantaan virus, alphaviruses, such as Semliki forest virus, epidemic hemorrhagic fever virus, polio virus or enteroviruses, such as ECHO 9, ECHO 12 and Coxsackie B3.

Antibodies or antibody fragments which are directed against membrane structures of muscle cells, in particular of smooth muscle cells, are examples of ligands for muscle cells. Examples of antibodies of this nature are antibody 10F3, antibodies against actin, antibodies against angiotensin II receptors, antibodies against receptors for growth factors or antibodies, for example, against EGF receptors, against PDGF receptors or against FGF receptors, or antibodies against endothelin A receptors.

The ligands furthermore include nucleotide sequences for active substances which bind to membrane structures or membrane receptors on muscle cells [Pusztai et al., J. Pathol. 169, 191 (1993), Harris, Curr. Opin. Biotechnol. 2, 260 (1991)]. Examples of these ligands are growth factors, or their fragments or part sequences thereof, which bind to receptors which are expressed in smooth muscle cells, for example PDGF, EGF, TGFβ, TGFα, FGF or endothelin A.

The ligands also include glycoproteins from the coats of those viruses which have a tropism for muscle cells. An example of these viruses is cytomegalovirus [Speir et al., Science 265, 391 (1994)].

Examples of ligands for activated macrophages and/or activated lymphocytes are, in addition, nucleotide sequences which encode substances which bind specifically to the surface of immune cells. These substances include antibodies or antibody fragments which are directed against membrane structures of immune cells, as have been described, for example, by Powelson et al., Biotech. Adv. 11, 725 (1993) and Barclay et al., The Leucocyte Antigen, Academic Press (1994). The ligands also include monoclonal or polyclonal antibodies or antibody fragments which bind, by their antigen-binding variable moiety, to Fcγ, Fcε or Fcµ receptors of immune cells [Rojanasakul et al., Pharm. Res. 11, 1731 (1994)]. They furthermore include the Fc fragment of human monoclonal or polyclonal immunoglobulin.

The ligands furthermore include all substances which bind to membrane receptors on the surface of immune cells. These substances include cytokines, such as IL-1, L-2, IL-3, IL-4, IL-6, IL-10, TNFα, GM-CSF and M-CSF, and also growth factors, such as EGF, TGF, FGF, IGF or PDGF, or their fragments or part sequences thereof, which bind to receptors which are expressed in immune cells [Callard et al., The Cytokine, Academic Press (1994)]. The ligands also include adhesion molecules and other ligands which bind to cell membrane structures on macrophages, and in spleen, liver, lung and other tissues [Pigott et al., The Adhesion Molecule, Academic Press (1994), Perales et al., Eur. J. Biochem. 226, 255 (1994)].

The ligands within the meaning of this invention also include glycoproteins from the coats of those viruses which have a tropism for lymphocytes and/or macrophages. Examples of these macrophage-infecting viruses are HIV-1, in particular those strains having mutations in the V3 region of gp120 which result in increased binding to macrophages, HIV-2, Hantaviruses, for example Punmalavirus, cytomegalovirus, respiratory syncytial virus, herpes simplex virus or filoviruses.

Examples of lymphocyte-infecting viruses are varicella zoster virus (VZV), since VZV infects T cells in particular, herpesvirus 6 (HHV 6), since HHV 6 likewise infects T cells in particular, rabies virus, since rabies virus coat protein binds to TH2 cells in particular, HIV-1, since glycoprotein gp120 binds preferably to the CD4 molecule of T cells, HTLV-II, since HTLV-II infects B cells in particular, HTLV-I, since HTLV-I infects T cells in particular, influenza C viruses, since influenza C viruses bind to N-acetyl-9-β-acetylneuraminic acid (Neu 5,9 Ac), which preferentially occurs on B lymphocytes and to a lesser extent, or not at all, on T lymphocytes, by way of the hemagglutininesterase fusion (HEF) protein, influenza C viruses having a mutation in nucleotide position 872, which encodes position 284 of the amino acid sequence of the HEF, for example with the threonine being replaced with isoleucine, since the surface protein HEF which possesses this mutation has a markedly stronger affinity for the N-acetyl-9-O-acetylneuraminic acid receptor than does the wild-type virus, cleavage products of the influenza C virus HEF which contain the structure for binding to N-acetyl-9-β-acetylneuraminic acid. This binding structure is defined by the catalytic triad serine 71, histidine 368 or 369 and aspartic acid 261, Epstein-Barr virus, since EBV infects B cells in particular, herpes simplex virus 2, since HSV-2 infects T cells in particular, or measles virus.

Examples of ligands for synovial cells and inflammatory cells which are to be mentioned are nucleic acid sequences which encode antibodies or antibody fragments which bind, by their variable domains, to membrane structures of synovial cells or inflammatory cells. Examples of these membrane structures are vimentin [Miettinen et al., Am. J. Pathol. 117, 18 (1984)], fibronectin [Wojciak et al., Clin. Exp. Immunol. 93, 108 (1993)] or Fc receptors. These ligands also include antibodies or antibody fragments which bind to the Fc receptor by their constant domains [Rojanasakul et al., Pharm. Res. 11, 1731 (1994)].

These ligands furthermore include all active compounds which bind to membrane structures or membrane receptors on synovial cells. Examples of these are cytokines or growth factors, or their fragments or part sequences thereof, which bind to receptors which are expressed by synovial cells, for example IL-1-RA, TNFα, IL-4, IL-6, IL-10, IGF or TGFβ [Callard et al., The Cytokine, Academic Press (1994)].

Examples of ligands for virus-infected cells which are to be mentioned are nucleic acid constructs which encode antibodies or antibody fragments which are directed against the viral antigens which are located on the cell membrane of virus-infected cells. Antibodies of this nature are directed, for example, against antigens of HBV, HCV, HSV, HPV, HIV, EBV or HTLV.

Examples of ligands for liver cells and other tissue cells are all substances which bind to membrane structures or membrane receptors on the surface of liver cells. Examples of these are growth factors, such as cytokines, EGF, TGF, FGF or PDGF, or their fragments or part sequences thereof, which bind to receptors which are expressed in cells of this nature.

These ligands furthermore include ligands which bind to cell membrane structures which are selective for particular tissues. Examples are:

| | Ligand | Tissue cells |
|---|---|---|
| Transferrin receptor | Transferrin | Liver, other tissue cells |
| Insulin receptor | Insulin | Liver, other tissue cells |
| Fcγ receptors | Immunoglobulin G | Reticuloendothelial system, other tissue cells |

These ligands and membrane structures are reviewed in Perales et al., Eur. J. Biochem. 226, 255 (1994).

The ligands particularly include glycoproteins from the coats of viruses which have a tropism for selected cells, such as for bronchial epithelial cells (respiratory syncytial virus), liver cells (hepatitis C virus), filoviruses, Marburg virus by way of the asialoglycoprotein receptor of liver cells, hepatitis B virus, with liver cells preferably binding to the preS2 and preS1 domains of HBV by way of the asialoglycoprotein receptor, hepatitis D virus, liver-sinusoidal cells, and heptatis B virus, with HBV being bound by way of fibronectin.

Examples of ligands for glia cells are nucleic acid sequences which encode antibodies or antibody fragments which are directed against membrane structures of glia cells, as have been reported, for example, by Mirsky et al. [Cell and Tissue Res. 240, 723 (1985)], Coakham et al. [Prog. Exp. Tumor Res. 29, 57 (1985)] and McKeever et al. [Neurobiol. 6, 119 (1991)]. These membrane structures furthermore include neural adhesion molecules such as N-CAM, in particular its polypeptide chain C [Nybroe et al., J. Cell Biol. 101, 2310 (1985)]. These ligands furthermore include all active compounds which bind to membrane structures or membrane receptors on glia cells. Examples of these active compounds are insulin and insulin-like growth factor, and those fragments of these growth factors which bind to the relevant membrane receptors.

The ligands within the meaning of the invention additionally include nucleic acid sequences which encode glycoproteins of the coats of those viruses which have a tropism for glia cells.

These viruses include, for example, HIV-1 subtype JRF1 or herpes simplex virus I.

Examples of ligands for leukemia cells include nucleic acid constructs which encode antibodies or antibody fragments which are directed against membrane structures of leukemia cells. A large number of monoclonal antibodies of this nature have already been described for diagnostic and therapeutic procedures [Kristensen, Danish Medical Bulletin 41, 52 (1994); Schranz, Therapia Hungarica 38, 3 (1990); Drexler et al., Leuk. Res. 10, 279 (1986); Naeim, Dis. Markers 7, 1 (1989); Stickney et al., Curr. Opin. Oncol. 4, 847 (1992); Drexler et al., Blut 57, 327 (1988); Freedman et al., Cancer Invest. 9, 69 (1991)]. Depending on the type of leukemia, monoclonal antibodies, or their antigen-binding antibody fragments, of the following specificity are, for example, suitable as ligands:

AML cells having the membrane antigens CD13, CD14, CD15, CD33, CAMAL and sialosyl-Le; B-CLL cells having the membrane antigens CD5, CD1c and CD23, and also idiotypes and isotypes of the membrane immunoglobulins T-CLL cells having the membrane antigens CD33, M38, IL-2 receptors and T cell receptors; and ALL cells having the membrane antigens CALLA and CD19, and also non-Hodgkin's lymphoma.

The ligands furthermore include all active compounds which bind to membrane structures or membrane receptors of leukemia cells. Examples of these are growth factors, or their fragments or part sequences thereof, which bind to receptors which are expressed in leukemia cells.

Growth factors of this nature have already been described [reviews in Cross et al., Cell 64, 271 (1991); Aulitzky et al., Drugs 48, 667 (1994); Moore, Clin. Cancer Res. 1, 3 (1995); Van Kooten et al., Leuk. Lymph. 12, 27 (1993)]. For example, they include IFNα, in the case of non-Hodgkin's lymphomas, IL-2, particularly in the case of T cell leukemias, FGF in the case of T cell, monocytic, myeloid, erythrocytic and megakaryoblastic leukemias, TGFβ in the case of leukemias, or retinoids, e.g. retinoic acid, in the case of acute promyelocytic leukemia.

Examples of ligands for tumor cells include nucleic acid sequences which encode antibodies, and fragments of these antibodies, which are directed against membrane structures on tumor cells. Antibodies of this nature have been reviewed, for example, by Sedlacek et al., Contrib. to Oncol. 32, Karger Verlag, Munich (1988) and Contrib. to Oncol. 43, Karger Verlag, Munich (1992).

Other examples are antibodies against sialyl Lewis, peptides on tumors which are recognized by T cells, proteins expressed by oncogenes, gangliosides such as GD3, GD2, GM2, 9-O-acetyl-GD3 and fucosyl-GM1, blood group antigens and their precursors, antigens on polymorphic epithelial mucine or antigens on heat shock proteins.

Nucleic Acid Sequence [Component b)] Which Encodes an Active Compound (Protein B)

The active compound (protein B) according to the present invention can be a substance which, for example, intervenes in a biological activation cascade and/or is an active component of this cascade. These substances include active compounds which activate the coagulation cascade, for example thrombin [MacGillivray et al., Ann. N.Y. Acad. Sci. 485, 73 (1986)], thrombin which is mutated in the region of the Arg-Thr cleavage site (amino acid position 327/328), factor Va [Cripe et al., Biochem. 31, 3777 (1992), Jenny et al., PNAS-U.S.A. 84, 4846 (1987)], factor VIIa [O'Hara et al., PNAS-U.S.A. 84, 5158 (1987)], factor IXa [Yoshitake et al., Biochem. 24, 3736 (1985)], factor Xa [Messier et al., Gene 99, 291 (1991)] or tissue factor and coagulation-active fragments thereof [Morrissey et al., Cell 50, 29 (1987); Scarpati et al., Biochem. 26, 5234 (1987); Spicer et al., PNAS-U.S.A. 84, 5148 (1987); Rehemtulla et al., Thromb. Heamost. 65, 521 (1991)] or which inhibit the coagulation cascade or which activate fibrinolysis, for example the plasminogen activator inhibitors PAI-1, PAI-2 and PAI-3, hirudin, protein C, serine proteinase inhibitors, such as C-1S inhibitor, α1-antitrypsin or antithrombin III, tissue factor pathway inhibitor (TFPI), plasminogen activators such as urokinase, tissue plasminogen activator (tPA), or hybrids thereof, or which activate the complement cascade, for example cobra venom factor (CVF) or part sequences of CVF which correspond functionally to human complement factor C3b, i.e. which are able to bind to complement factor B and which, after having been cleaved by factor D, constitute a C3 convertase (the DNA sequence for CVF and its part sequences were described by Fritzinger et al., Proc. Natl. Acad. Sci. U.S.A. 91, 12775 (1994)), human complement factor C3b (the DNA sequence for C3 and its part sequences were published by De Bruijn et al., Proc. Natl. Acad. Sci. U.S.A. 82, 708 (1985), cleavage products of human complement factor C3 which resemble CVF functionally and structurally (such cleavage products have been described by O'Keefe et al., J. Biol. Chem. 263, 12690 (1988) or which activate the kinin system, the complement system and/or the coagulation system, for example activated Hagemann factor (F XIIa) [Shibuya et al., Biochem, Biophys. Acta 1206, 63 (1994), Que et al., Biochem. 25, 1525 (1986), Tripodi et al., Nucl. Acid Res. 14, 3146 (1986)] or kallikrein [Chen et al., Biochem. J. 307, 481 (1995), Fukushima et al., Biochem. 24, 8037 (1985)].

The active compound (protein B) can also be a cytostatic, cytotoxic or inflammation-eliciting protein, such as perforin, granzyme, cytokines, such as IL-1, IL-2, TL-4, IL-12, IL-3, IL-5, human leukemia inhibitory factor (LIF), IL-7, IL-11, IL-13, GM-CSF, G-CSFb or M-CSF, interferons, such as IFNα, IFNβ or IFNγ, TNF, such as TNFα or TNFβ, oncostatin M, sphingomyelinase [Jarvis et al., PNAS U.S.A. 91, 73 (1994)], magainin and magainin derivatives [Cruciani et al., PNAS U.S.A. 88, 3792 (1991)]; Jacob et al., Ciba Found. symp. 186, 197 (1994); Peck-Miller et al., Cancer Chemother. Pharmac. 32, 109 (1993)] or chemokines, such as RANTES (MCP-2), monocyte chemotactic and activating factor (MCAF), IL-8, macrophage inflammatory protein 1 (MIP-1α or MIP-1β) or neutrophil activating protein 2 (NAP-2).

The active compound (protein B) can also be an antiangiogenic protein, such as angiostatin, interferons, such as IFNα, IFNβ or IFNγ, platelet factor 4, IL-12, TIMP-1, TIMP-2 or TIMP-3.

The active compound (protein B) can also be an enzyme which is able to convert an inactive precursor of a pharmacological active substance, for example a cytostatic agent, into the active substance itself. Examples of such active compounds are bacterial nitroreductase, bacterial β-glucuronidase, plant β-glucuronidase derived from Secale cereale, human β-glucuronidase, human carboxypeptidase (CB), e.g. mast cell CB-A or pancreas CB-B, or bacterial carboxypeptidase, bacterial β-lactamase, bacterial cytosine deaminase, human catalase or peroxidase, phosphatase, in particular human alkaline phosphatase or human acid prostate phosphatase, type 5 acid phosphatase, oxidase, in particular human lysyl oxidase or human acid D-aminooxidase, peroxidase, in particular human glutathione peroxidase, human eosinophilic peroxidase or human thyroid peroxidase.

The active compound (protein B) can also be a protein which affects the immune system, for example a protein having an antiallergic effect, such as IFNβ, IFNγ, IL-10, soluble IL-4 receptors, IL-12 or TGFβ, or a protein which can prevent the rejection of transplanted organs, such as IL-10, TGFβ, soluble IL-1 receptors, soluble IL-2 receptors, IL-2 receptor antagonists or soluble IL-6 receptors, or a protein for the therapy of antibody-mediated autoimmune diseases, for example TGFβ, IFNα, IFNβ, IFNγ, IL-12, soluble IL-4 receptors or soluble IL-6 receptors, or a protein for the therapy of cell-mediated autoimmune diseases, for example IL-6, IL-9, IL-10, IL-13, TNFα, IL-4 or TNFβ, or a protein for the therapy of arthritis. According to the present invention, structural genes can also be selected whose expressed protein directly or indirectly inhibits inflammation, for example in a joint, and/or promotes the reconstitution of extracellular matrix (cartilage and connective tissue) in the joint. These expressed proteins include, for example, IL-1 receptor antagonists (IL-1-RA), since IL-1-RA inhibits the binding of IL-1α and IL-1β, soluble IL-1 receptor, since soluble IL-1 receptor binds and inactivates IL-1, IL-6, since IL-6 increases secretion of TIMP and superoxides and decreases secretion of IL-1 and TNFα by synovial cells and chondrocytes, soluble TNF receptor, since soluble TNF receptor binds and activates TNF, IL-4, since IL-4 inhibits the formation and secretion of IL-1, TNFα and MMP, IL-10, since IL-10 inhibits the formation and secretion of IL-1, TNFα and MMP and increases the secretion of TIMP, insulin-like growth factor (IGF-1), since IGF-1 stimulates the synthesis of extracellular matrix, TGFβ, especially TGFβ1 and TGFβ2, since TGFβ stimulates the synthesis of extracellular matrix superoxide dismutase, or TIMP (tissue inhibitors of metalloproteinases), especially TIMP-1, TIMP-2 or TIMP-3.

The active compound (protein B) can also be a protein for relieving damage to the nervous system, for example a growth factor, such as FGF, nerve growth factor (NGF), brain-derived neurotrophic factor (BDNF), neurotrophin 3 (NT-3), neurotrophin 4 (NT-4) or ciliary neurotrophic factor (CNTF), or a cytokine, or a cytokine inhibitor, which is able to inhibit or neutralize the neurotoxic effect of TNFα, for example TGFβ, soluble TNF receptors, IL-10, since IL-10 inhibits the formation of IFNγ, TNFα, IL-2 and IL-4, soluble IL1 receptors, such as IL-1 receptor I or IL-1 receptor II, since soluble IL-1 receptors neutralize the activity of IL-1, IL-1 receptor antagonist or soluble IL-6 receptors.

The active compound (protein B) can also be a protein which stimulates angiogenesis, for example VEGF or FGF.

The active compound (protein B) can furthermore be a protein which lowers blood pressure, for example kallikrein or endothelial cell nitric oxide synthase.

The active compound (protein B) can also be a protein for the therapy of chronic infectious diseases, for example a protein which exhibits cytostatic or cytotoxic effects, or an enzyme which cleaves a precursor of an antiviral or cytotoxic substance into the active substance, or a cytotoxin having an antiviral effect or a growth factor having an antiviral effect. Examples are IFNα, IFNβ, IFNγ, TNFβ, TNFα, IL-1 or TGFβ.

The present invention furthermore relates to a nucleic acid construct in which two identical or two different DNA sequences, which encode identical or different active compounds (protein B) [component b) and b")] are combined.

In order to ensure that both DNA sequences are expressed, the cDNA of an internal ribosome entry site (IRES) is preferably intercalated, as a regulatory element, between the two structures. An internal ribosome entry site makes it possible to express two DNA sequences which are linked to each other by way of an IRES. IRESs of this nature have been described, for example, by Montford and Smith TIG 11, 179 (1995); Kaufman et al., Nucl. Acids Res. 19, 4485 (1991); Morgan et al., Nucl. Acids Res. 20, 1293 (1992); Dirks et al., Gene 128, 247 (1993); Pelletier and Sonenberg, Nature 334, 320 (1988) and Sugitomo et al., BioTechn. 12, 694 (1994). Thus, for example, the cDNA for the polio virus IRES sequence (positions≦140 to ≧630 of the 5' UTR [Pelletier and Sonenberg, Nature 334, 320 (1988)] can be used to link the DNA of component c) to the DNA of component d).

Nucleic Acid Sequences [Component c)] Which Encode the Protease-Cleavable Part Structure C According to the present invention, part stucture C comprises an amino acid sequence which is cleaved by proteases which are formed in tumors or by tumor cells or inflammatory cells. The nucleic acid sequence for this part structure C is inserted, for example, into the nucleic acid sequence of the naturally occurring precursor (protein BSD, where S is the naturally occurring cleavage sequence) of the relevant active compound (protein B) in place of the cleavage sequence S such that this recombinant nucleic acid expresses protein BCD or B'BCD.

The nucleic acid sequence encoding part structure C is chosen depending on the protease which is predominantly secreted in the tumor or in the inflammation.

The following part structures C may, for example, be employed for the following enzymes [Barrett et al., Mammalian Proteases, Academic Press, London (1980), Panchal et al., Nature Biotechnol. 14, 852 (1996); Pigott et al., Ayad et al., The extracellular Matrix, Academic press (1994); Yoshida et al., Int. J. Cancer 63, 863 (1995), Petersen et al., J. Biol. Chem. 265, 6104 (1990); Cramer et al., J. Urology 156, 526 (1995); Forsgen et al., FEBS Lett. 213, 254 (1987) Zhang et al. Chin. Chem. 41, 1567, (1995)]:

| | | | | | | | Part structure C cleavage | |
|---|---|---|---|---|---|---|---|---|
| Enzyme | A6 | A5 | A4 | A3 | A2 | A1 | A-1 | (A-2) |
| Plasminogen activator (SEQ ID NOS 4–8, respectively) | | | | Cys | Pro | Gly | Arg | Val (Ile) | (Val) |
| | | | | | Gln | Gly | Arg | | |
| | | | | | Gly | Gly | Arg | | |
| | | | | Pro | Arg | Phe | Lys | | |
| | | | | | Gly | Lys | Arg | | |
| Prostrate-specific antigen (SEQ ID NOS 9–20, respectively) | | | | Pro | Arg | Phe | Lys | Ile | (Ile) (Val) |
| | | | | | Arg | Pro | Tyr | | |
| | | | | Arg | Arg | Phe | Phe | Leu (Ile) | (His) (Val) |
| | | | | | | | Tyr | Ile | Val |
| | Ser | Phe | Ser | Ile | Gln | Tyr | Ile | Val | |
| | Gly | Ser | Gln | Gln | Leu | Leu | Ile | Val | |
| | Gly | Ile | Ser | Ser | Gln | Tyr | Ile | Val | |

-continued

| Enzyme | A6 | A5 | A4 | A3 | A2 | A1 | Part structure C cleavage A-1 | (A-2) |
|---|---|---|---|---|---|---|---|---|
| Cathepsins (SEQ ID NOS 21–34, respectively) | | | | Pro | Arg | Phe | Lys | Ile | Ile (Val) |
| | | | | | | | Tyr | | |
| | | | | | Lys | Ser | Arg | Met (Ile) | |
| | | | | | Lys | Met | Arg | Arg (Ile) | |
| | | | | | Ile | Arg | Arg | Arg (Ile) | |
| | | | | | Arg | Ala | Arg | Leu (Ile) | |
| | | | | | Gln | Ala | Arg | Phe (Ile) | |
| | | | | | Lys | Leu | Arg | Leu (Ile) | |
| | | | | | | Lys | Arg | Val (Ile) | |
| | | | | | | | Lys | | |
| | | | | | | Phe | Arg | | |
| Stromelysins (SEQ ID NOS 35–44, respectively) | | | | Gly | Gly | Gly | Ala | Gln | (Leu) |
| | | | | Gln | Leu | Gly | Val | Met | (Gln) |
| | | | | Ala | Ala | Ala | Ser | Leu | (Lys) |
| | | | | Val | Ala | Val | Ser | Ala | (Lys) |
| | | | | Leu | Ala | Ala | Asn | Leu | (Arg) |
| Collagenase I (SEQ ID NOS 45–48, respectively) | | | | Gly | Pro | Gln | Gly | Ile | (Ala) |
| | | | | Gly | Pro | Gln | Gly | Leu | (Leu) |
| II (SEQ ID NOS 49–50, respectively) | | | | Gly | Pro | Gln | Gly | Leu | (Ala) |
| III (SEQ ID NOS 51–52, respectively) | | | | Gly | Ile | Ala | Gly | Ile | (Thr) |
| VIII (SEQ ID NOS 53–56, respectively) | | | | Gly | Leu | Pro | Gly | Ile | (Gly) |
| | | | | Gly | Phe | Pro | Gly | Ile | (Gly) |
| XI (SEQ ID NOS 57–60, respectively) | | | | Gly | Pro | Ala | Gly | Ile | (Ser) |
| | | | | Gly | Pro | Ala | Gly | Ile | (Ala) |
| Plasminogen (SEQ ID NOS 61–62, respectively) | | | | Ser | Gly | Thr | Glu | Ile | (Val) |

The amino acid positions (A1–A6 and A-1 and A-2) were defined in accordance with Schechter and Bergr, Biochem. Biophys. Res. Comm. 27, 157 (1967).

Nucleic Acid Sequences [component d)] Which Encode Part Structure D

According to the present invention, the nucleic acid sequence [component d)] encodes a peptide (part structure D) which binds to the active compound (part structure B) by way of the part structure C and inactivates this active compound by means of this binding.

Preferably, those nucleic acid sequences are used for part structure D which encode part structure D in the naturally occurring precursors (protein BSD), with part structure S being the natural cleavage sequence in protein BSD.

The structures of the naturally occurring precursors of active compounds (protein B) have already been reviewed, for example by Bartett et al., Mammalian Proteases, Academic Press, London (1980) in the case of coagulation factors, complement factors and kallikrein, by Callard et al., The Cytokine Facts Book, Academic Press (1994) in the case of interleukins, chemokines and growth factors, and by Denhardt et al., Pharmac. Ther. 59, 329 (1993) in the case of tissue inhibitors of metalloproteinases (TIMPs).

When selecting active compounds which do not have any naturally occurring precursors, and in the case of xenogeneic active compounds, use should be made of nucleic acid sequences, as component d), which encode any peptide, preferably, however, of nucleic acid sequences which encode those part structures D which naturally occur in the precursors of human active compounds.

In order to facilitate secretion of the protein BCD, or B'BCD, which is expressed by the novel nucleic acid sequence, the homologous signal sequence which may be present in the DNA sequence of component b) can be replaced with a heterologous signal sequence which improves extracellular secretion. Thus, for example, the signal sequence for immunoglobulin [DNA positions≦63 to ≧107; Riechmann et al., Nature 332, 323 (1988)] or the signal sequence for CEA [DNA positions≦33 to ≧134, Schrewe et al., Mol. Cell Biol. 10, 2738 (1990); Berling et al., Cancer Res. 50, 5634 (1990)] or the signal sequence of human respiratory syncytial virus glycoproteins [cDNA of amino acids≦38 to ≧50 or 48 to 65; Lichtenstein et al., J. Gen. Virol. 77, 109 (1996)] can be inserted.

In addition, in order to augment translation, the nucleotide sequence GCCACC or GCCGCC [Kozak, J. Cell Biol. 108, 299 (1989)] can be inserted at the 3' end of the promoter sequence and directly at the 5' end of the start signal (ATG) of the signal sequence.

Preparation of the Novel Nucleic Acid Constructs

The novel nucleic acid constructs which have been described are prepared by linking the individual components to each other using standard molecular biological methods.

Applications

The novel nucleic acid construct is particularly well suited for treating diseases which are accompanied by an increased local formation of proteases, such as tumor diseases, leukemias, allergies, autoimmune diseases, infections, inflammations, transplant rejection reactions, thromboses and blood vessel occlusions and other disturbances of blood clotting and of blood circulation, and tissue injuries, including injuries to the central nervous system and damage to the nervous system. Administration is effected locally (e.g. onto the skin), nasally, orally, gastrointestinally, intrabronchially, intravesically, intravaginally, into the uterus, subcutaneously, intramuscularly, periarticularly, intraarticularly, into the cerebrospinal fluid, into the brain tissue, into the spinal medulla, into wounds, intraperitoneally or intrapleurally, or systemically, e.g. intravenously, intraarterially, intraportally or into the heart.

In general, the administered composition comprises, where appropriate in addition to the customary additives and auxiliary substances, either the novel nucleic acid construct or a cell which is able to express the novel nucleic acid construct. The administered composition can be administered for the prophylaxis or therapy of a disease, as already described in detail above.

For administration purposes, an effective amount is determined by the skilled artisan considering variables well known in the art such as the nature of the applicable disease or condition, the nature of the patient, mammal or cells being treated and the method of administration.

Moreover, in addition to the methods of administration discussed above, the present invention contemplates the administration of the novel nucleic acid construct to a mammal by ex viva gene transfer of the cells of the subject mammal in a clinical setting. Such techniques are well known to those of skill in the art. In addition, the present invention contemplates introduction of the novel nucleic acid construct into cells in vivo [Rosenberg et al., *Science* 242:1575–1578 (1988) and Wolff et al., *PNAS* 86:9011–9014 (1989)]. In this regard, the routes of delivery include systemic administration and administration in situ. Well-known techniques include systemic administration with cationic liposomes, and administration in situ with viral vectors. Any one of the gene delivery methodologies described in the existing art is suitable for the introduction of novel nucleic acid construct into a target cell.

Said cell is prepared, for example, by transforming or transfecting cells with the novel nucleic acid construct using methods known to the skilled person.

Examples of suitable cells are endothelial cells, lymphocytes, macrophages, glia cells, fibroblasts, liver cells, kidney cells, muscle cells, cells of the bone or cartilage tissue, synovial cells, peritoneal cells, skin cells, epithelial cells, leukemia cells and/or tumor cells.

The novel cells are also suitable for preparing the protein which is encoded by the novel nucleic acid construct and which can be used directly as a drug.

The present invention furthermore relates, therefore, to the use of the novel nucleic acid construct for preparing a recombinantly altered cell, with the nucleic acid construct being introduced into the cells, to the use of the novel nucleic acid construct for preparing a protein which is encoded by the nucleic acid construct, with the nucleic acid construct being caused to express in a suitable cell and the protein which is formed being isolated, and to a cell which harbors the novel nucleic acid construct. The above-described cells are the preferred cells.

The following selection can, for example, be made from the above-mentioned examples of promoter sequences and structural genes (for the protein BCD or B'BCD) depending on the nature and site of the disease and on the target cell to be transduced:

Therapy of Tumors

Promoters [component a)]: endothelial cell-specific and cell cycle-specific or cell-nonspecific or muscle cell-specific and cell cycle-specific or tumor cell-specific (solid tumors, leukemias)

Ligands for the following target cells [component b')]: proliferating endothelial cells or stroma cells and muscle cells adjacent to the endothelial cell or tumor cells or leukemia cells.

Structural genes [component b)c)d)]: for coagulation-inducing factors, for complement factors, for angiogenesis inhibitors, for cytostatic and cytotoxic proteins, for inducers of inflammations or for enzymes for activating precursors of cytostatic agents, for example for enzymes which cleave inactive precursor substances (prodrugs) thereby forming active cytostatic agents (drugs).

Therapy of Autoimmune Diseases and Inflammations

Promoters [component a)] : endothelial cell-specific and cell cycle-specific, or macrophage-specific and/or lymphocyte-specific and/or cell cycle-specific or synovial cell-specific and/or cell cycle-specific.

Ligands for the following target cells [component b')]: proliferating endothelial cells, macrophages and/or lymphocytes or synovial cells.

Structural genes [component b)c)d)]: for the therapy of antibody-mediated autoimmune diseases, for inhibitors of cell proliferation, cytostatic or cytotoxic proteins, enzymes for activating precursors of cytostatic agents or for the therapy of arthritis.

Therapy of Damage to the Nervous System

Promoters [component a)]: glia cell-specific, endothelial cell-specific and cell cycle-specific or nonspecific and cell cycle-specific.

Ligands for the following target cells [component b')]: glia cells or proliferating endothelial cells Structural genes [component b)c)d)]: for neuronal growth factors, for example for cytokines and cytokine inhibitors which inhibit or neutralize the neurotoxic effect of TNFα.

Therapy of disturbances of the blood coagulation system and the blood circulation system:

Promoters [component a)]: cell-nonspecific, cell-nonspecific and cell cycle-specific or specific for endothelial cells, smooth muscle cells or macrophages, or specific for endothelial cells, smooth muscle cells or macrophages and cell cycle-specific.

Ligands for the following target cells [component b')] : endothelial cells, proliferating endothelial cells or somatic cells in the vicinity of endothelial cells and smooth muscle cells or macrophages.

Structural genes [component b)c)d)]: for the inhibition of coagulation or for the promotion of fibrinolysis, for angiogenesis factors, for hypotensive peptides, for an antiproliferative, cytostatic or cytotoxic protein or for an enzyme for cleaving precursors of cytostatic agents, thereby forming cytostatic agents, for inhibition of the proliferation of smooth muscle cells following injury to the endothelial layer or for blood plasma proteins, such as C1 inactivator, serum cholinesterase or α1-antitrypsin.

Therapy of Chronic Infectious Diseases

Promoters [component a)]: virus-specific, cell-specific or virus-specific or cell-specific and cell cycle-specific.

Ligands for the following target cells [component b')]: liver cells, lymphocyte and/or macrophage, epithelial cell or endothelial cell.

Structural genes [components b)c)d)]: or a protein which exhibits cytostatic or cytotoxic effects, an enzyme which cleaves a precursor of an antiviral or cytotoxic substance thereby forming the active substance, or for antiviral proteins such as antivirally active cytokines and growth factors.

The invention is explained in more detail with the aid of the following examples and figures without restricting it thereto:

EXAMPLES

1. Preparation of a Nucleic Acid Construct Encoding Prostate-Specific Antigen (PSA)-Activatable FX This deals with the preparation of a therapeutic agent for treating prostate carcinoma metastases. Despite the surgical removal of a prostate which has become carcinomatous, metastases of the prostate carcinoma frequently arise which are currently still largely untreatable and which lead to the death of the patient. Such prostate carcinoma metastases induce angiogenesis. Furthermore, prostate carcinoma metastases secrete a tissue-specific enzyme, i.e. prostate-specific antigen (PSA). In accordance with the invention, a nucleic acid construct is prepared which, having been introduced into proliferating endothelial cells, leads to a modified FX coagulation factor being expressed. The modification comprises replacing, in the gene for the natural FX, the nucleotide sequence for the natural cleavage site, whose cleavage results in coagulation-active FXa, with a nucleotide sequence encoding a PSA-specific cleavage site. As a result, the PSA which is secreted by prostate carcinoma metastases is able to specifically activate the modified FX which is secreted by proliferating endothelial cells in the vicinity of the metastases and thereby to initiate the coagulation which leads to the blood supply to the metastasis being interrupted and consequently to necrosis of the metastasis.

The nucleic acid construct for the PSA-activatable FX is prepared in accordance with a scheme which is depicted in FIG. 3.

The DNA sequences of the individual components are joined together, in the 5' to 3' direction, as follows:

Component a), which contains the promoter sequence of the cdc25C gene [nucleic acids: −290 to +121; Lucibello et al., EMBO J. 14, 132 (1995); Zwicker et al., Nucl. Acids Res. 23, 3822 (1995); EMBO J. 14, 4514 (1995)], the sequence GCCACC (Kozak, J. Cell Biol. 108, 229 (1989)) and the cDNA for the immunoglobulin signal peptide [nucleotide sequence ≦63 to ≧107; Riechmann et al., Nature 332, 323 (1988)], is fused to component b)c)d), which contains the cDNA for human FX (nucleotide sequence 1 to ≧1468) [Messier et al., Gene 99, 291 (1991)] in which amino acid 194 has been mutated from Arg to Tyr.

The individual components of the construct are linked by way of suitable restriction sites which are introduced at the termini of the different elements by way of PCR amplification. The linking is effected using enzymes which are specific for the restriction sites and which are known to the skilled person, and DNA ligases. These enzymes can be obtained commercially.

The nucleotide construct which has been prepared in this way is cloned into pUC 18/19 or Bluescript-derived plasmid vectors.

2. Expression in Human Embryonic Kidney Cells

Proliferating human embryonic kidney cells [HEK 293; Racchi et al., J. Biol. Chem. 268, 5735 (1993)] which are being maintained in culture are transfected with the above-described plasmid using the method known to the skilled person [Graham and van der Eb, Virol. 52, 456 (1973)].

The mutated factor X is purified from the supernatant from approx. $10^7$ transfected HEK 293 cells [Watzke et al., J. Clin. Invest. 88, 1685 (1991)] and assayed in a coagulation test for factor X with and without the addition of PSA. Purified PSA is obtained from Chemicon (Temecula, Calif., U.S.A.).

In this test, the coagulation defect in human FX-deficient plasma is counterbalanced by functionally active FXa.

Nonmutated (wild-type) FX (which is activated by Russel's viper venom) is employed as a positive control. In addition to the test mixture lacking PSA, a mock preparation from the supernatant from untransfected HEK 293 cells is used as a negative control.

The coagulation activity of the mutated FX is measured by recalcification time (Seitz R et al., Int. J. Cancer 53:514–520, 1993). 100 μl of FX-deficient plasma (Behringwerke, Marburg) are incubated, at 37° C. for 120 sec, with 100 μl of the FX preparation from the cell supernatant. The FX preparation contains PSA as activator. No PSA is added in the case of the negative control. FX (wild-type) and Russel's viper venom (RVV) are employed as the positive control. The coagulation reaction is augmented by adding 100 μl of 0.02 M CaCl2 and determined in a coagulometer.

The following results are obtained:

The negative controls without any activation of coagulation give a coagulation time of approx. 200 sec. By contrast, significantly shorter coagulation times, of 50 sec, are achieved when activated FX (mutated FX and PSA or wild-type FX and RVV) is used.

It can be concluded from this that the transduced HEK 293 cells express mutated FX which, in the added presence of PSA, counterbalances the coagulation defect of FX-deficient plasma.

3. Expression in Human Endothelial Cells

Human umbilical cord endothelial cells which are being maintained in culture are transfected with the above-described plasmid using the method known to the skilled person (Lucibello et al., EMBO J. 14, 132 (1995).

In order to check cell cycle specificity, endothelial cells are synchronized in G0/G1 by withdrawing methionine over a period of 48 hours. After staining with Hoechst 33258 (Hoechst AG, Frankfurt), the DNA content of the cells is determined in a fluorescent-activated cell sorter (Lucibello et al., EMBO J. 14, 132 (1995).

The expression of the nucleic acid construct is assayed in the supernatant from the endothelial cells in analogy with the investigation carried out on the HEK 293 cells.

The following results are obtained:

The protein which is expressed by the transfected endothelial cells counterbalances the coagulation defect of FX-deficient plasma, in contrast to mock preparations from the supernatant from untransfected endothelial cells.

A markedly higher concentration of mutated FX can be detected in the supernatant from proliferating, transduced endothelial cells (DNA>2S) as compared with the supernatant from endothelial cells which have been synchronized in G0/G1 (DNA=2S).

Consequently, the above-described nucleic acid construct leads to the gene for the mutated FX being expressed in a cell cycle-dependent manner in endothelial cells, and this mutated FX can be activated by PSA such that it brings about coagulation in FX-deficient plasma.

Federal Republic of Germany priority application, DE 19701141.1, filed Jan. 16, 1997, including the specification, drawings, claims and abstract, is hereby incorporated by reference.

---

What is claimed is:

1. An isolated nucleic acid construct for expressing a biologically active substance which is activated by an enzyme which is released from mammalian cells, wherein said construct comprises the following nucleic acid sequences in the following order:
   a) at least one promoter element operably linked to;
   b) at least one nucleic acid sequence which encodes a biologically active compound, wherein said active compound is endogenous to mammals, operably linked to;
   c) at least one nucleic acid sequence which encodes an amino acid sequence cleavable specifically by a protease which is released from a mammalian cell, operably linked to;
   d) at least one DNA sequence which encodes a polypeptide which is bound to said active compound by said cleavable amino acid sequence and inhibits the activity of said active compound, and wherein said nucleic acid component c) does not naturally occur as operably linking said nucleic acid sequence b) to said nucleic acid d).

2. A nucleic acid construct as claimed in claim 1, wherein said protease is a prostate specific antigen, a plasminogen activator, a cathepsin or a matrix metalloproteinase.

3. A nucleic acid construct as claimed in claim 1, wherein said mammalian cells are tumor cells, leukemia cells, endothelial cells, macrophages, lymphocytes, muscle cells, epithelial cells, glia cells, synovial cells or virus-infected cells.

4. A nucleic acid construct as claimed in claim 1, wherein said nucleic acid construct further comprises a nucleic acid sequence operably linked to said construct of claim 1, wherein said nucleic acid sequence encodes a ligand which binds said active compound to a target structure.

5. A nucleic acid construct as claimed in claim 1, wherein said nucleic acid sequences b) and d) of claim 1 encode parts of a natural precursor of a biologically active protein compound, wherein the nucleic acid sequence encoding the cleavage sequence naturally occurring between said nucleic acid sequences b) and d) has been replaced by said nucleic acid sequence c), which does not naturally occur between said nucleic acid sequences b) and d).

6. A nucleic acid construct as claimed in claim 1, wherein said polypeptide encoded by said nucleic acid sequence d) is part of a natural precursor of a biologically active protein compound.

7. A nucleic acid construct as claimed in claim 1, wherein said construct is operably inserted into a plasmid or a viral vector.

8. A nucleic acid construct as claimed in claim 1, wherein said nucleic acid sequence a) is a promoter sequence which can be activated nonspecifically, cell-specifically, virus-specifically, metabolically, cell cycle-specifically or by tetracycline.

9. A nucleic acid construct as claimed in claim 1, wherein said nucleic acid sequence a) comprises at least two identical or two different promoter sequences.

10. A nucleic acid construct as claimed claim 8, wherein said nucleic acid sequence a) is activated in endothelial cells, in cells adjoining activated endothelial cells, in muscle cells, in leukemia cells, in tumor cells, in glia cells, in lymphocytes, in macrophages or in synovial cells.

11. A nucleic acid construct as claimed in claim 1, wherein said active compound activates or inhibits a biological activation cascade or is an active component of this cascade, or activates or inhibits the coagulation system, activates fibrinolysis, activates the complement system or activates the kinin system, or is an enzyme which converts the inactive precursor of a pharmacological substance into the pharmacologically active substance, or which itself is a pharmacologically active substance.

12. A nucleic acid construct as claimed in claim 11, wherein said active compound is a coagulation factor selected from the group consisting of thrombin, factor Va, factor VIIa, factor IXa, factor Xa, TF coagulation-active fragments and factor XIIa; thrombin which is mutated in the region of the Arg-Thr cleavage site at amino acid position 327/328; a fibrinolytic protein selected from the group consisting of urokinase, tPA and functional hybrids thereof; a complement factor selected from the group consisting of CVF, C3b and functional cleavage products thereof; an antithrombotic protein selected from the group consisting of protein C, C-1S inhibitor, α1-antitrypsin, hirudin, AT-III, TFPI, PAI-1, PAI-2 and PAI-3; a kallikrein; a cytostatic, cytotoxic or inflammation-eliciting protein; an antiangiogenic protein; an immunomodulatory protein; an antiinflammatory protein; a protein which relieves damage to the nervous system; a protein which inhibits or neutralizes the neurotoxic effect of TNFα; an angiogenesis-stimulating protein; a hypotensive protein; an antiviral protein; a cytokine; an interferon; a tumor necrosis factor; oncostatin M or LIF; a cytokine receptor; the moiety of a cytokine receptor which is external to the cell; a cytokine antagonist; a growth factor; a growth factor receptor; the moiety of a growth factor receptor which is external to the cell; a chemokine; angiostatin; platelet factor 4; TIMP-1, TIMP-2 or TIMP-3; a nitroreductase; a β-glucuronidase; a carboxypeptidase; a β-lactamase; a cytosine deaminase; a catalase; a peroxidase; a phosphatase; an oxidase; kallikrein or an endothelial cell nitric oxide synthase.

13. A nucleic acid construct as claimed in claim 1, which further comprises a nucleic acid sequence b') which encodes a ligand which binds to a cell membrane receptor, a cell membrane antigen, a cell membrane-located adhesion molecule, or to the extracellular matrix or component thereof.

14. A nucleic acid construct as claimed in claim 13, wherein said ligand is an antibody or an antibody fragment which binds specifically to a cell membrane antigen or to an antigen on the extracellular matrix, or is a polypeptide which binds to receptor on the cell membrane wherein said polypeptide is a growth factor, a cytokine, an interferon, a tumor necrosis factor, a chemokine, a receptor-binding part sequence of these ligands, a peptide hormone, angiotensin, kinin, folic acid, an adhesion molecule or the part sequence of the adhesion molecule which binds to the corresponding adhesion molecule or to the extracellular matrix, an extracellular moiety of an Fc receptor, a glycoprotein of a virus, a part sequence of the glycoprotein which binds to these cells, the transmembrane domain of a receptor or of a viral glycoprotein, or a glycophospholipid anchor.

15. A nucleic acid construct as claimed in claim 13, wherein said ligand binds to activated or proliferating endothelial cells, to tumor cells, to muscle cells, preferably smooth muscle cells, to fibroblasts, to macrophages, to lymphocytes, to liver cells, to kidney cells, to synovial cells, to inflammatory cells, to virus-infected cells, to bronchial epithelial cells, to glia cells or to leukemia cells.

16. A nucleic acid construct as claimed in claim 13, wherein the construct comprises at least two identical or different nucleic acid sequences b)c)d) or b')b)c)d), which nucleic acid sequences are linked to each other by way of an internal ribosomal entry site.

17. A process for preparing a nucleic acid construct according to claim 1, which comprises operably linking said nucleic acid sequences of claim 1.

18. A method for preparing a recombinantly altered cell, comprising transducing a suitable cell with said nucleic acid construct of claim 1.

19. A method for preparing a polypeptide which is encoded by said nucleic acid construct of claim 1, comprising transducing a suitable cell with said construct, expressing said polypeptide in said cell, and isolating said expressed polypeptide.

20. The method of claim 18, wherein said cell is an endothelial cell, a lymphocyte, a macrophage, a glia cell, a fibroblast, a liver cell, a kidney cell, a muscle cell, a cell of the bone or cartilage tissue, a synovial cell, a peritoneal cell, a skin cell, an epithelial cell, a leukemia cell or a tumor cell.

21. The method of claim 19, wherein said cell is an endothelial cell, a lymphocyte, a macrophage, a glia cell, a fibroblast, a liver cell, a kidney cell, a muscle cell, a cell of the bone or cartilage tissue, a synovial cell, a peritoneal cell, a skin cell, an epithelial cell, a leukemia cell or a tumor cell.

22. A cell transduced with said nucleic acid construct of claim 1.

* * * * *